US007883703B2

(12) United States Patent
Weiner et al.

(10) Patent No.: US 7,883,703 B2
(45) Date of Patent: Feb. 8, 2011

(54) METHODS OF MODULATING IMMUNITY

(75) Inventors: Howard L. Weiner, Brookline, MA (US); Mohamed H. Sayegh, Westwood, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1221 days.

(21) Appl. No.: 10/987,380

(22) Filed: Nov. 12, 2004

(65) Prior Publication Data

US 2005/0196395 A1 Sep. 8, 2005

Related U.S. Application Data

(60) Provisional application No. 60/520,148, filed on Nov. 14, 2003, provisional application No. 60/567,741, filed on May 3, 2004.

(51) Int. Cl.
*A61K 39/395* (2006.01)
(52) U.S. Cl. .................. 424/144.1; 424/154.1; 514/825; 514/863; 514/866; 514/885; 514/903
(58) Field of Classification Search .................. None
See application file for complete search history.

(56) References Cited

U.S. PATENT DOCUMENTS

| | | | |
|---|---|---|---|
| 4,361,549 A | 11/1982 | Kung et al. | |
| 4,515,893 A | 5/1985 | Kung et al. | |
| 4,654,210 A | 3/1987 | Kung et al. | |
| 5,556,763 A | 9/1996 | Ochoa et al. | |
| 5,658,570 A | 8/1997 | Newman et al. | |
| 5,681,722 A | 10/1997 | Newman et al. | |
| 5,693,780 A | 12/1997 | Newman et al. | |
| 5,711,937 A | 1/1998 | Nishida et al. | |
| 5,750,105 A | 5/1998 | Newman et al. | |
| 5,756,096 A | 5/1998 | Newman et al. | |
| 5,834,597 A | 11/1998 | Tso et al. | |
| 6,030,613 A * | 2/2000 | Blumberg et al. | 424/134.1 |
| 6,090,380 A | 7/2000 | Weisbart | |
| 6,143,297 A | 11/2000 | Bluestone | |
| 6,197,328 B1 | 3/2001 | Yanagawa | |
| 6,406,696 B1 | 6/2002 | Bluestone | |
| 6,576,651 B2 | 6/2003 | Bandyopadhyay et al. | |
| 7,041,289 B1 * | 5/2006 | Bach et al. | 424/133.1 |
| 2002/0150580 A1 | 10/2002 | Newman et al. | |
| 2003/0235536 A1* | 12/2003 | Blumberg et al. | 424/45 |
| 2005/0042664 A1* | 2/2005 | Wu et al. | 435/6 |
| 2007/0117778 A1 | 5/2007 | Ilan | |

FOREIGN PATENT DOCUMENTS

| | | |
|---|---|---|
| JP | 2002-506420 | 2/2002 |
| JP | 2002-542205 | 12/2002 |
| WO | WO 90/08540 | 8/1990 |
| WO | WO 93/02108 | 2/1993 |
| WO | WO 9814209 A1 * | 4/1998 |
| WO | WO 9847531 A2 * | 10/1998 |
| WO | WO 01/37860 | 5/2001 |
| WO | WO 0130300 A2 * | 5/2001 |
| WO | WO 0154721 A1 * | 8/2001 |
| WO | WO 01/94419 | 12/2001 |
| WO | WO03009812 A2 | 2/2003 |
| WO | WO 03026692 A2 * | 4/2003 |
| WO | WO03067221 A2 | 8/2003 |
| WO | WO03068934 A2 | 8/2003 |
| WO | WO2005048935 A2 | 6/2005 |
| WO | WO2009090656 A2 | 7/2009 |

OTHER PUBLICATIONS

Utset, J Rheumatol. Sep. 2002;29(9):1907-13.*
De Kozak et al., Int Rev Immunol. Mar.-Jun. 2002;21(2-3):231-53.*
Groux et al., Nature. Oct. 16, 1997;389(6652):737-42.*
Del Zotto et al., Clin Exp Immunol. Oct. 2003;134(1):120-6.*
Selman et al., Ann Intern Med. Jan. 16, 2001;134(2):136-51.*
Chen et al., J Immunol. Dec. 1, 2002;169(11):6530-8.*
Czernok et al., Clin Exp Immunol. Jul. 1996;105(1):104-11.*
Johansson et al., Curr Opin Infect Dis. Feb 2003;16(1):43-9.*
Heldin et al., Cell. Jan 27, 1995;80(2):213-23.*
Kozlowski et al., Acta Neuropathol. 1987;74(2):163-8.*
Utset et al., J Rheumatol 2002;29:1907-13.*
Appelbaum, "Haematopoietic cell transplantation as immunotherapy," *Nature*, 411:385-389 (2001).
Barnes et al., "A randomised trial of oral gammaglobulin in low-birth-weight infants infected with rotavirus," *Lancet*, 1(8286):1371-1373 (1982).
Belghith et al., "TGF-β-dependent mechanisms mediate restoration of self-tolerance induced by antibodies to CD3 in overt autoimmune diabetes," *Nat. Med.*, 9(9):1202-1208 (2003).
Chatenoud, "CD3-specific antibody-induced active tolerance: from bench to bedside," *Nat. Rev. Immunol.*, 3:123-132 (2003).
Chatenoud et al., "CD3 Antibody-Induced Dominant Self Tolerance in Overtly Diabetic NOD Mice," *J. Immunol.*, 158:2947-2954 (1997).
Cleland et al., "Mucosal tolerance and rheumatoid arthritis," *Br. J. Rheumatol.*, 36(11):1139-1141 (1997).
Cosimi et al., "Treatment of acute renal allograft rejection with OKT3 monoclonal antibody," *Transplantation*, 32(6):535-539 (1981).
Cosimi et al., "Use of monoclonal antibodies to T-cell subsets for immunologic monitoring and treatment in recipients of renal allografts," *N. Engl. J. Med.*, 305(6):308-314 (1981).
Herold et al., "Anti-CD3 monoclonal antibody in new-onset type 1 diabetes mellitus," *N. Engl. J. Med.*, 346(22):1692-1698 (2002).
Hill et al., "T-Helper 1—Type Immunity to Trophoblast in Women With Recurrent Spontaneous Abortion," *JAMA*, 273(24):1933-1936 (1995).
Iijima et al., "Mucosal immune network in the gut for the control of infectious diseases," *Rev. Med. Virol.*, 11:117-133 (2001).

(Continued)

*Primary Examiner*—Zachary Skelding
(74) *Attorney, Agent, or Firm*—Fish & Richardson P.C.

(57) ABSTRACT

The invention provides novel methods of administering anti-CD3 antibodies, e.g., via oral or mucosal delivery. The invention also provides methods of treating, preventing, or delaying the onset of autoimmune disorders by oral or mucosal administration of anti-CD3 antibodies. Finally, the invention provides compositions including anti-CD3 antibodies, suitable for oral or mucosal administration.

16 Claims, 21 Drawing Sheets

OTHER PUBLICATIONS

Jameson, "Maintaining the Norm: T-Cell Homeostasis," *Nat. Rev. Immunol.*, 2(8):547-556 (2002).
Londei et al., "Efficient Propagation and Cloning of Human T Cells in the Absence of Antigen by Means of OKT3, Interleukin 2, and Antigen-Presenting Cells," *Scand. J. Immunol.*, 27:35-46 (1988).
Lu et al., "A Novel Population of Expanded Human CD3+CD56+ Cells Derived from T Cells with Potent In Vivo Antitumor Activity in Mice with Severe Combined Immunodeficiency," *J. Immunol.*, 153(4):1687-1696(1994).
MacLean et al., "T Cell-dependent Regulation of Eotaxin in Antigen-induced Pulmonary Eosinophila," *J. Exp. Med.*, 184(4):1461-1469 (1996).
"Orthoclone OKT3 Prescribing Information—Clinical Pharmacology," Ortho Biotech Products, L.P., http://healthcareprofessionals.orthobiotech.com/products/orthoclone/pi_pharmacology.jsp, 2 pages (Jun. 2, 2003).
"Orthoclone OKT3 Prescribing Information—Description," Ortho Biotech Products, L.P., http://healthcareprofessionals.orthobiotech.com/products/orthoclone/pi_description.jsp, 1 page (Jun. 2, 2003).
"Orthoclone OKT3 Prescribing Information—Dosage and Administration," Ortho Biotech Products, L.P., http://healthcareprofessionals.orthobiotech.com/products/orthoclone/pi_dosage.jsp, 2 pages (Jun. 2, 2003).
Pacyna et al., "Survival of Rotavirus Antibody Activity Derived From Bovine Colostrum After Passage Through the Human Gastrointestinal Tract," *J. Pediatr. Gastroenterol. Nutr.*, 32(2):162-167 (2001).
Petrovsky et al., "Prospects for the Prevention and Reversal of Type 1 Diabetes Mellitus," *Drugs*, 62(18):2617-2635 (2002).
Reilly et al., "Oral Delivery of Antibodies: Future Pharmacokinetic Trends," *Clin. Pharmacokinet.*, 32(4):313-323 (1997).
Salles et al., "Changes in the leucocyte subpopulations of the palatine tonsillar crypt epithelium of pigs in response to *Streptococcus suis* type 2 infection," *Vet. Immunol. Immunopathol.*, 87:51-63 (2002).
Seung et al., "Allogeneic hematopoietic chimerism in mice treated with sublethal myeloablation and anti-CD154 antibody: absence of graft-versus-host disease, induction of skin allograft tolerance, and prevention of recurrent autoimmunity in islet-allografted NOD/Lt mice," *Blood*, 95(6):2175-2182 (2000).
Tran et al., "Reversal of experimental allergic encephalomyelitis with non-mitogenic, non-depleting anti-CD3 mAb therapy with a preferential effect on $T_h1$ cells that is augmented by IL-4," *Int. Immunol.*, 13(9):1109-1120 (2001).
Viglietta et al., "Loss of Functional Suppression by CD4+CD25+ Regulatory T Cells in Patients with Multiple Sclerosis," *J. Exp. Med.*, 199(7):971-979 (2004).
Weiner, "Current Issues in the Treatment of Human Diseases by Mucosal Tolerance," *Ann. N.Y. Acad. Sci.*, 1029:211-224 (2004).
Weiner, "Immunosuppressive treatment in multiple sclerosis," *J. Neurol. Sci.*, 223:1-11 (2004).
Weiner, "Multiple Sclerosis Is an Inflammatory T-Cell—Mediated Autoimmune Disease," *Arch. Neurol.*, 61:1613-1615 (2004).
Weiner, "Oral tolerance, an active immunologic process mediated by multiple mechanisms," *J. Clin. Invest.*, 106(8):935-937 (2000).
Weinshenker et al., "An open trial of OKT3 in patients with multiple sclerosis," *Neurology*, 41(7):1047-1052 (1991).
Wilson et al., "Multiple differences in gene expression in regulatory Vα24JαQ T cells from identical twins discordant for type I diabetes," *Proc. Natl. Acad. Sci. USA*, 97(13):7411-7416 (2000).
Faria et al., "Oral tolerance: mechanisms and therapeutic applications," *Adv. Immunol.*, 73:153-164 (1999).
Goldstein et al., "A randomized clinical trial of OKT-3 monoclonal antibody for acute rejection of cadaveric renal transplants," *New England Journal of Medicine*, 313(6): 337-342 (1985).
Ishikawa et al., "Inhibition of autoimmune diabetes by oral administration of anti-CD3 monoclonal antibody," *Diabetes*, 56(8):2103-2109 (2007).
Maron et al., "Regulatory Th2-type T cell lines against insulin and GAD peptides derived from orally- and nasally-treated NOD mice suppress diabetes," *J. Autoimmun.*, 12(4):251-258 (1999).
Ochi et al., "Oral CD3-specific antibody suppresses autoimmune encephalomyelitis by inducing CD4+ CD25− LAP+ T cells," *Nat. Med.*, 12(6):627-635 (2006).
Slavin et al., "Mucosal administration of IL-10 enhances oral tolerance in autoimmune encephalomyelitis and diabetes," *Int. Immunol.*, 13(6):825-833 (2001).
Abramowicz et al., "Release of tumor necrosis factor, interleukin-2, and gamma-interferon in serum after injection of OKT3 monoclonal antibody in kidney transplant recipients," Transplantation, 47(4):606-608 (1989).
Alegre et al., "Hypothermia and hypoglycemia induced by anti-CD3 monoclonal antibody in mice: role of tumor necrosis factor," Eur J Immunol, 20(3):707-710 (1990).
Chatenoud et al., "The anti-CD3-induced syndrome: a consequence of massive in vivo cell activation," Curr Top Microbiol Immunol, 174:121-134 (1991).
Chatenoud et al., "Corticosteroid inhibition of the OKT3-induced cytokine-related syndrome—dosage and kinetics prerequisites," Transplantation, 51(2):334-338 (1991).
Ferran et al., "Cytokine-related syndrome following injection of anti-CD3 monoclonal antibody: further evidence for transient in vivo T cell activation," Eur J Immunol, 20(3):509-515 (1990).
Friend et al., "Phase I Study of an Engineered Aglycosylated Humanized CD3 Antibody in Renal Transplant Rejection," Transplantation, 68(11):1632-1637 (1999).
Hirsch et al., "Effects of in vivo administration of anti-CD3 monoclonal antibody on T cell function in mice. II. In vivo activation of T cells," J Immunol, 142(3):737-743 (1989).
Ilan et al., "Induction of regulatory T cells decreases adipose inflammation and alleviates insulin resistance in ob/ob mice," Proc Natl Acad Sci U S A, 107(21):9765-9770 (2010).
Keymeulen et al., "Insulin needs after CD3-antibody therapy in new-onset type 1 diabetes," N Engl J Med, 352 (25):2598-608 (2005).
Lockoff, "Glycolipids as Immunomodulators Syntheses and Properties," Angewandte Chemie, International Edition, 30(12):1611-1620 (1991).
Ochi et al., "New immunosuppressive approaches: oral administration of CD3-specific antibody to treat autoimmunity," J. Neurol. Sci., 274:9-12 (2008).
Sasaki et al., "Oral anti-CD3 antibody treatment induces regulatory T cells and inhibits the development of atherosclerosis in mice," Circulation, 120(20):1996-2005 (2009).
Stuenkel et al., "Synthetic Glycolipids with Immunopotentiating activity on humoral immunity: evaluation in vivo," Progress in Leukocyte Biology, 9(1):575-579 (1988).
Van Wauwe et al., "OKT3: a monoclonal anti-human T lymphocyte antibody with potent mitogenic properties," J Immunol., 124(6):2708-2713 (1980).
Woodle et al., "Phase I Trial of a Humanized, Fc Receptor NonBinding OKT3 Antibody, huOKT3y1 (Ala-Ala) in the Treatment of Acute Renal Allograft Rejection," Transplantation, 68(5):608-616 (1999).
Wu et al., "Suppression of murine SLE by oral anti-CD3: inducible CD4+CD25−LAP+ regulatory T cells control the expansion of IL-17+ follicular helper T cells," 18(7):586-96 (2009).
Wu et al., "Nasal Anti-CD3 Antibody Ameliorates Lupus by Inducing an IL-10-Secreting CD4+CD25−LAP+ Regulatory T Cell and Is Associated with Down-Regulation of IL-17+CD4+ICOS+CXCR5+ Follicular Helper T Cells1," J Immunol., 181:6038-6050 (2008).
International Search Report dated Dec. 9, 2009 issued in PCT/IL2009/000072.
Chatenoud et al., "Anti-CD3 antibody induces long-term remission of overt autoimmunity in nonobese diabetic mice," Proceedings of the National Academy of Sciences of the United States of America, 91(1):123-127 (1994).
Ortho Multicenter Transplant Study Group, "A Randomized Clinical Trial of OKT3 Monoclonal Antibody for Acute Rejection of Cadaveric Renal Transplants," The New England Journal of Medicine, 313(6):337-342 (1985).
Tran et al., "Reversal of experimental allergic encephalomyelit is with non-mitogenic, non-depleting anti-CD3 mAb therapy with a preferential effect on Th1 cells that is augmented by IL-4," International Immunology, 13(9):1109-1120 (2001).
Herold et al., "Anti-CD3 Monoclonal Antibody in New-Onset Type 1 Diabetes Mullitus," The New England Journal of Medicine, 346(22):1692-1698 (2000).

* cited by examiner

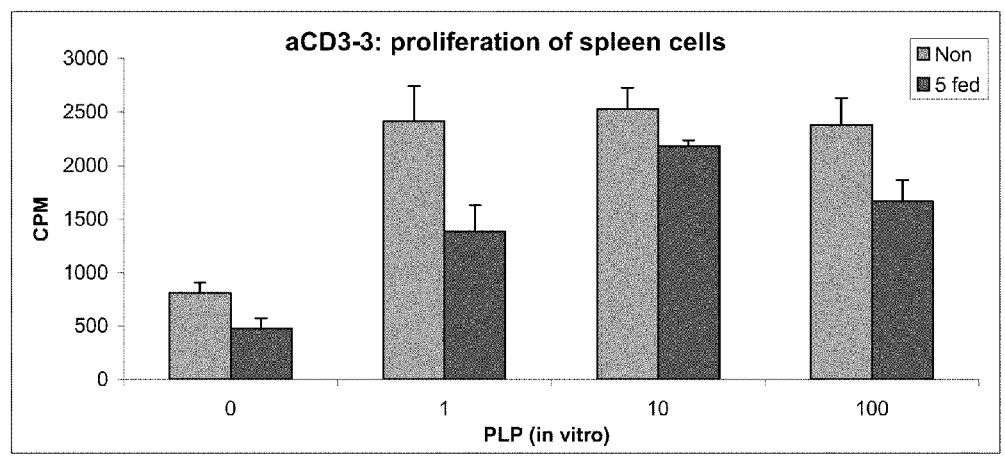
Figure 3
Figure 4
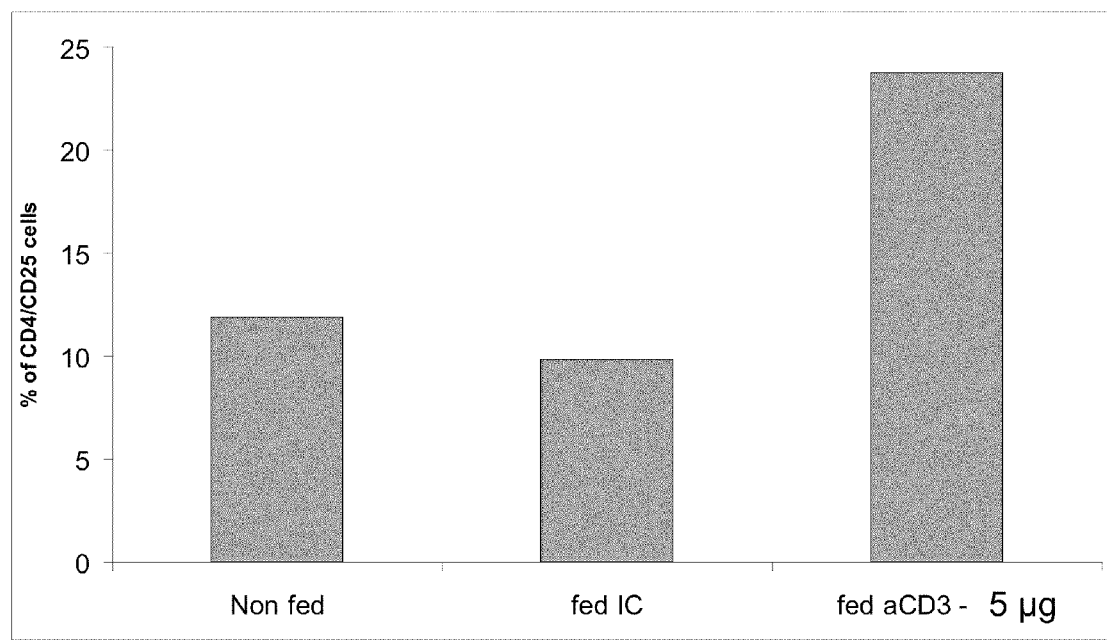

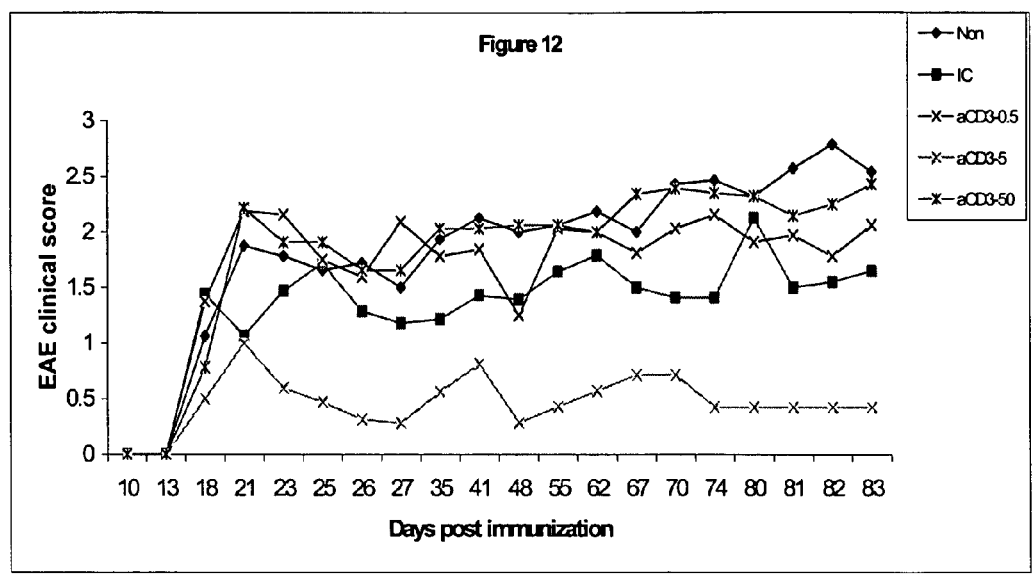

METHODS OF MODULATING IMMUNITY

CLAIM OF PRIORITY

This application claims the benefit under 35 USC §119(e) of U.S. Provisional Patent Application Ser. Nos. 60/520,148, filed on Nov. 14, 2003 and 60/567,741, filed on May 3, 2004, the entire contents of which are hereby incorporated by reference.

FEDERALLY SPONSORED RESEARCH OR DEVELOPMENT

This invention was made with Government support under Grants Nos. NS-38037-01 and AI-435801, awarded by the National Institutes of Health. The Government has certain rights in the invention.

TECHNICAL FIELD

Described herein are methods for the treatment of autoimmune diseases and preventing allograft rejection, particularly the treatment of autoimmune diseases via oral or mucosal administration of antibodies that leads to stimulation of the mucosal immune system, e.g., anti-CD3 antibodies.

BACKGROUND

Immunotherapy strategies that involve antibody-induced signaling through antigen-specific T-cell receptors (TCR) have been shown to ameliorate autoimmune disease, probably by regulating the immune response to self-antigens. Parenterally administered anti-CD3 monoclonal antibody (mAb) therapy in particular has been shown to be efficacious in preventing and reversing the onset of diabetes in NOD mice (Chatenoud et al., J. Immunol. 158:2947-2954 (1997); Belghith et al., Nat. Med. 9:1202-1208 (2003)) and in treating subjects with Type I diabetes (Herold et al., N. Engl. J. Med. 346(22)1692-1698 (2002), and to reverse experimental allergic encephalomyelitis (EAE) in Lewis rats with a preferential suppressive effect on T-helper type 1 (Th1) cells, which participate in cell-mediated immunity (Tran et al., Intl. Immunol. 13(9): 1109-1120 (2001)). The FDA has approved Orthoclone OKT®3 (muromonab-CD3; Ortho Biotech Products, Bridgewater, N.J.), a murine anti-CD3 antibody, for intravenous injection for the treatment of graft rejection after transplantation (Chatenoud, Nat. Rev. Immunol. 3:123-132 (2003)).

SUMMARY

The present invention is based in part on the discovery that oral administration of anti-CD3 monoclonal antibody is efficacious in treating and preventing autoimmune disease. As described herein, the oral administration of anti-CD3 antibody suppresses experimental allergic encephalomyelitis (EAE, an animal model of multiple sclerosis (MS)), delays allograft rejection in a dose-dependent fashion, reduces the severity of arthritis, and prevents the onset of diabetes in the NOD mouse. Thus, the invention provides novel methods of administering anti-CD3 antibodies, e.g., via oral or mucosal delivery. The invention also provides methods of treating or preventing autoimmune disorders, e.g., a cell-mediated or antibody-mediated autoimmune diseases, and of preventing allograft rejection, by oral or mucosal administration of anti-CD3 antibodies, e.g., whole antibodies or active fragments thereof (e.g., F(ab')$_2$). Further, the invention provides compositions that contain anti-CD3 antibodies and are suitable for oral or mucosal administration.

In one aspect, the invention provides methods of treating or preventing an autoimmune disease, or preventing allograft rejection, in a subject by administering to the subject an anti-CD3 antibody or active fragment thereof (e.g., F(ab')$_2$). The antibody can be administered orally or mucosally, e.g., via pulmonary, buccal, nasal, intranasal, sublingual, rectal, or vaginal administration. Autoimmune diseases that can be treated in this manner include multiple sclerosis, type I diabetes, graft-versus-host disease, rheumatoid arthritis, psoriasis, inflammatory bowel disease, uveitis, and thyroiditis. In addition, a number of autoimmune diseases that may be treated using the methods described herein are described in Rose and Mackay, *The Autoimmune Diseases* (Academic Press, San Diego, Calif. 1998).

In another aspect, the invention provides methods for preventing allograft rejection in a subject. The methods include administering to the subject an anti-CD3 antibody, wherein the administering is oral or mucosal, e.g., pulmonary, buccal, nasal, intranasal, sublingual, rectal, or vaginal. In some embodiments, the anti-CD3 antibody is administered to the subject before, during, and/or after transplanting a cell, tissue or organ to the subject. In some embodiments, the transplant comprises all or part of a pancreatic islet, liver, kidney, heart, lung, skin, muscle, neuronal tissue, stomach, and intestines.

In another aspect, the invention provides pharmaceutical compositions suitable for oral or mucosal administration including an anti-CD3 antibody. In some embodiments, the pharmaceutical composition is suitable for pulmonary, buccal, nasal, intranasal, sublingual, rectal, or vaginal administration. In some embodiments, the anti-CD3 antibody is selected from the group consisting of a murine monoclonal antibody, a humanized antibody, a human antibody, and a chimeric antibody. In some embodiments, the composition suitable for oral administration is in a form selected from a liquid oral dosage form and a solid oral dosage form, e.g., selected from the group consisting of tablets, capsules, caplets, powders, pellets, granules, powder in a sachet, enteric coated tablets, enteric coated beads, encapsulated powders, encapsulated pellets, encapsulated granules, and enteric coated soft gel capsules. In some embodiments, the oral dosage form is a controlled release oral formulation.

In some embodiments, the pharmaceutical compositions further comprise excipients and/or carriers. In some embodiments, the pharmaceutical compositions further comprise additional active ingredients.

In an additional aspect, the invention provides methods of providing an anti-CD3 antibody to a subject. The methods can include administering to the subject an oral dosage form suitable to deliver a dosage of an anti-CD3 antibody via the gastrointestinal tract, which, upon oral administration, leads to stimulation of the mucosal immune system. In another embodiment, the methods include administering to the subject a mucosal dosage form suitable to deliver a dosage of an anti-CD3 antibody via a mucous membrane, which, upon mucosal administration, leads to stimulation of the mucosal immune system.

In a further aspect, the invention provides methods of providing an anti-CD3 antibody to a subject. The methods include administering to the subject an oral dosage form suitable to deliver a dosage of an anti-CD3 antibody via the gastrointestinal tract, which, upon oral mucosal administration, leads to depletion of CD3+ cells in serum to less than about 25 cells/mm$^3$.

The invention provides several advantages. First, oral or mucosal administration is easier and is generally preferred over parenteral administration (e.g., intravenous or by injection) by the majority of subjects, due to the lack of needles. Second, oral or mucosal administration facilitates chronic administration of the antibody. Third, oral or mucosal administration can avoid or reduce the negative side effects associated with parenteral administration, including injection site pain. Other advantages include reduced costs, since highly trained personnel are not required for oral or mucosal administration, and fewer safety concerns. In some circumstances orally or mucosally administered anti-CD3 antibodies induce tolerance at a lower dosage than parenterally administered anti-CD3 antibodies. Moreover, oral or mucosal antibodies can be effective when administered before development of the disease and when given at the peak of the disease, while parenterally administered antibodies are commonly believed to be effective only after onset of the disease (Chatenoud et al., J. Immunol. 158: 2947-2954 (1997); Tran et al., Int. Immunol. 13: 1109-1120 (2001)). The gut and mucosal immune system is a unique environment that preferentially induces tolerance and regulatory T cells (Faria and Weiner, Adv. Immunol. 73:153-264 (1999)). Finally, oral or mucosal tolerance is systemic tolerance; for example, although the induction of oral tolerance occurs in the gut, peripheral tolerance also results (Faria and Weiner, Adv. Immunol. 73:153-264 (1999); Mowat, Nat. Rev. Immunol. 3(4):331-41 (2003)).

In some embodiments, in place of or in addition to the administration of an anti-CD3 antibody, the methods include the administration of one or more of a) antibodies against co-stimulatory molecules known to be involved in immune regulation such as CD2, ICOS, CD28, CTLA-4, and PD-1 or their ligands; b) antibodies against molecules associated with NK-T cells such as CD94, NK G2; c) antibodies against MHC molecules or their recognition structures such as CD4 and CD8; d) T cell differentiation molecules as TIM molecules; and/or e) any antibodies or combination thereof that either activate or promote tolerance.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3 is a bar graph illustrating the proliferation of spleen cells isolated from SJL mice fed 5 µg anti-CD3 antibody and immunized with PLP peptide (139-151), in response to stimulation with the PLP peptide.

FIG. 4 is a bar graph illustrating the proportion of CD4+/CD25+ T cells in mesenteric lymph nodes (MLN) isolated from SJL mice fed 5 µg anti-CD3 or isotype-matched control.

FIG. 12 is a line graph illustrating the course of EAE in MOG-immunized NOD mice fed 0.5, 5, or 50 µg anti-CD3 antibody.

DETAILED DESCRIPTION

Figure 1:
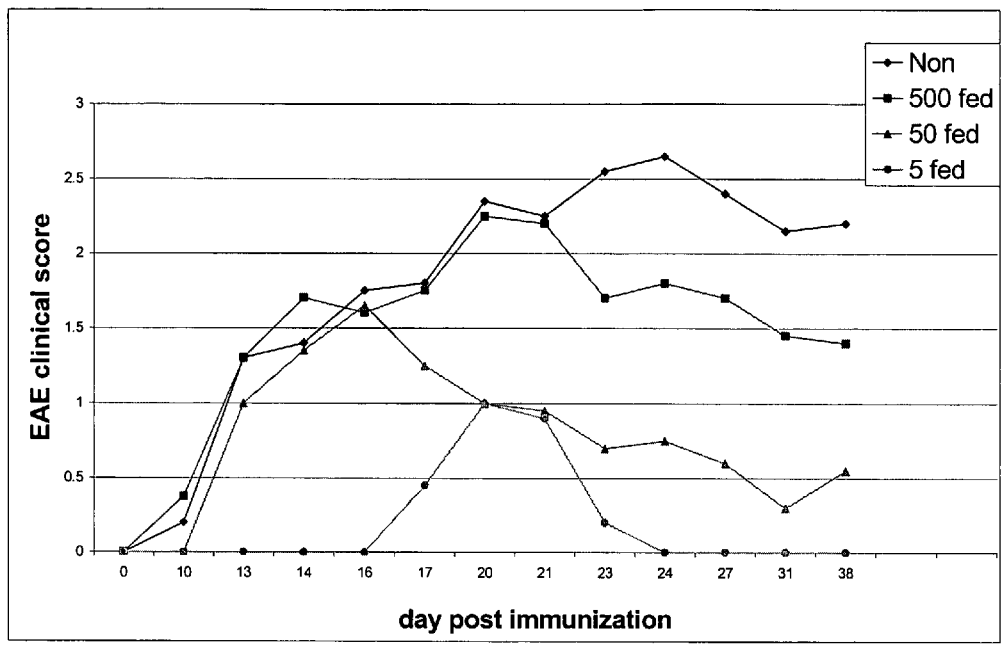
FIG. 1 is a line graph illustrating the course of EAE in SJL mice immunized with PLP (139-151) peptide and fed 5, 50, or 500 µg anti-CD3 antibody.

Anti-CD3 antibodies have been shown to be effective in treating a number of autoimmune disorders, both in animal models and in humans. For example, anti-CD3 antibodies have been shown to reverse graft rejection, probably by blocking the function of T cells which play a major role in acute allograft rejection. Previously, anti-CD3 antibody therapy has been administered parenterally (i.e., administered intravenously or by injection), based on the prevailing wisdom that the antibodies would be degraded, decomposed, or deactivated in the gastrointestinal tract and thus rendered useless if administered orally.

The present invention provides methods of treating autoimmune diseases via oral or mucosal administration of anti-CD3 antibodies and compositions suitable for oral or mucosal administration of anti-CD3 antibodies.

The usefulness of an oral formulation requires that the active agent be bioavailable. Bioavailability of orally administered drugs can be affected by a number of factors, such as drug absorption throughout the gastrointestinal tract, stability of the drug in the gastrointestinal tract, and the first pass effect. Thus, effective oral delivery of an active agent requires that the active agent have sufficient stability in the stomach and intestinal lumen to pass through the intestinal wall. Many drugs, however, tend to degrade quickly in the intestinal tract or have poor absorption in the intestinal tract so that oral administration is not an effective method for administering the drug. Surprisingly, not only can anti-CD3 antibodies be administered orally, but it appears that oral administration is, in some aspects, superior to parenteral administration.

Within the immune system, a series of anatomically distinct compartments can be distinguished, each specially adapted to respond to pathogens present in a particular set of body tissues. One compartment, the peripheral compartment, comprises the peripheral lymph nodes and spleen; this compartment responds to antigens that enter the tissues or spread into the blood. A second compartment, the mucosal immune system, is located near the mucosal surfaces where most pathogens invade. The mucosal immune system has evolved antigen-specific tolerance mechanisms to avoid a deleterious immune response to food antigens and beneficial, commensal microorganisms, which live in symbiosis with their host, while still detecting and killing pathogenic organisms that enter through the gut. Generally speaking, the gut associated lymphoid tissue (GALT) is different from lymphoid tissue elsewhere; stimulation of the GALT preferentially induces regulatory cells. The cells from the gut lymphoid tissue secrete mainly TGF-β and IL-10, and the chance and the frequency of stimulating regulatory cells is higher in the gut.

Immune responses induced within one compartment are largely confined to that particular compartment. Lymphocytes are restricted to particular compartments by their expression of homing receptors that are bound by ligands, known as addressing, that are specifically expressed within the tissues of the compartment. Interestingly, tolerance induced in the mucosal compartment also applies to the peripheral compartment. For example, the feeding of ovalbumin (a strong parenteral antigen) is followed by an extended period during which the administration of ovalbumin by injection, even in the presence of adjuvant, elicits no antibody response in either the peripheral compartment or the mucosal compartment. In contrast, oral tolerance is a systemic tolerance; although the induction of oral tolerance occurs in the gut, peripheral tolerance also results.

As one theory, orally administered anti-CD3 antibodies stimulate the mucosal immune system. As noted above, the gut is a unique environment in which to induce tolerance. In comparison with parenterally administered antibodies, lower amounts of oral anti-CD3 antibodies are needed to induce tolerance, and oral antibodies can be effective when administered before development of the disease and when given at the peak of the disease, while parenterally administered antibodies are good only after onset of the disease.

Pharmaceutical compositions suitable for oral administration are typically solid dosage forms (e.g., tablets) or liquid preparations (e.g., solutions, suspensions, or elixirs). Solid dosage forms are desirable for ease of determining and administering dosage of active ingredient, and ease of administration, particularly administration by the subject at home. Liquid dosage forms also allow subjects to easily take the required dose of active ingredient; liquid preparations can be prepared as a drink, or to be administered, for example, by a naso-gastric tube.

Liquid oral pharmaceutical compositions generally require a suitable solvent or carrier system in which to dissolve or disperse the active agent, thus enabling the composition to be administered to a subject. A suitable solvent system is compatible with the active agent and non-toxic to the subject. Typically, liquid oral formulations use a water-based solvent.

The oral compositions can also optionally be formulated to reduce or avoid the degradation, decomposition, or deactivation of the active agent by the gastrointestinal system, e.g., by gastric fluid in the stomach. For example, the compositions can optionally be formulated to pass through the stomach unaltered and to dissolve in the intestines, i.e., enteric coated compositions.

One of ordinary skill in the art would readily appreciate that the pharmaceutical compositions described herein can be prepared by applying known pharmaceutical manufacturing procedures. Such formulations can be administered to the subject with methods well-known in the pharmaceutical arts. Thus, the practice of the present methods will employ, unless otherwise indicated, conventional techniques of pharmaceutical sciences including pharmaceutical dosage form design, drug development, and pharmacology, as well as of organic chemistry, including polymer chemistry. Accordingly, these techniques are within the capabilities of one of ordinary skill in the art and are explained fully in the literature (See generally, for example, Remington: The Science and Practice of Pharmacy, Nineteenth Edition. Alfonso R. Gennaro (Ed.): Mack Publishing Co., Easton, Pa., (1995), hereinafter Remington, incorporated by reference herein in its entirety).

Anti-CD3 Antibodies

The anti-CD3 antibodies can be any antibodies specific for CD3. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which retain the ability to bind CD3. Such fragments can be obtained commercially, or using methods known in the art. For example F(ab)$_2$ fragments can be generated by treating the antibody with an enzyme such as pepsin, a non-specific endopeptidase that normally produces one F(ab)2 fragment and numerous small peptides of the Fc portion. The resulting F(ab)2 fragment is composed of two disulfide-connected Fab units. The Fc fragment is extensively degraded and can be separated from the F(ab)2 by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50,00 Dalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, Ill.). In addition, commercially available services for generating antigen-binding fragments can be used, e.g., Bio Express, West Lebanon, N.H.

The antibody can be a polyclonal, monoclonal, recombinant, e.g., a chimeric, de-immunized or humanized, fully human, non-human, e.g., murine, or single chain antibody. In some embodiments the antibody has effector function and can fix complement. In some embodiments, the antibody has reduced or no ability to bind an Fc receptor. For example, the anti-CD3 antibody can be an isotype or subtype, fragment or other mutant, which does not support binding to an Fc receptor, e.g., it has a mutagenized or deleted Fc receptor binding region. The antibody can be coupled to a toxin or imaging agent.

A number of anti-CD3 antibodies are known, including but not limited to OKT3 (muromonab/Orthoclone OKT3™,
Ortho Biotech, Raritan, N.J.; U.S. Pat. No. 4,361,549); hOKT3γ1 (Herold et al., N. E. J. M. 346(22):1692-1698 (2002); HuM291 (Nuvion™, Protein Design Labs, Fremont, Calif.); gOKT3-5 (Alegre et al., J. Immunol. 148(11):3461-8 (1992); 1F4 (Tanaka et al., J. Immunol. 142:2791-2795 (1989)); G4.18 (Nicolls et al., Transplantation 55:459-468 (1993)); 145-2C11 (Davignon et al., J. Immunol. 141(6): 1848-54 (1988)); and as described in Frenken et al., Transplantation 51(4):881-7 (1991); U.S. Pat. Nos. 6,491,9116, 6,406,696, and 6,143,297).

Methods for making such antibodies are also known. A full-length CD3 protein or antigenic peptide fragment of CD3 can be used as an immunogen, or can be used to identify anti-CD3 antibodies made with other immunogens, e.g., cells, membrane preparations, and the like, e.g., E rosette positive purified normal human peripheral T cells, as described in U.S. Pat. Nos. 4,361,549 and 4,654,210. The anti-CD3 antibody can bind an epitope on any domain or region on CD3.

Chimeric, humanized, de-immunized, or completely human antibodies are desirable for applications which include repeated administration, e.g., therapeutic treatment of human subjects.

Chimeric antibodies contain portions of two different antibodies, typically of two different species. Generally, such antibodies contain human constant regions and variable regions from another species, e.g., murine variable regions. For example, mouse/human chimeric antibodies have been reported which exhibit binding characteristics of the parental mouse antibody, and effector functions associated with the human constant region. See, e.g., Cabilly et al., U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397, all of which are incorporated by reference herein. Generally, these chimeric antibodies are constructed by preparing a genomic gene library from DNA extracted from pre-existing murine hybridomas (Nishimura et al., Cancer Research, 47:999 (1987)). The library is then screened for variable region genes from both heavy and light chains exhibiting the correct antibody fragment rearrangement patterns. Alternatively, cDNA libraries are prepared from RNA extracted from the hybridomas and screened, or the variable regions are obtained by polymerase chain reaction. The cloned variable region genes are then ligated into an expression vector containing cloned cassettes of the appropriate heavy or light chain human constant region gene. The chimeric genes can then be expressed in a cell line of choice, e.g., a murine myeloma line. Such chimeric antibodies have been used in human therapy.

Humanized antibodies are known in the art. Typically, "humanization" results in an antibody that is less immunogenic, with complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either (a) by grafting the entire nonhuman variable domains onto human constant regions to generate a chimeric antibody (Morrison et al., Proc. Natl. Acad. Sci., USA 81:6801 (1984); Morrison and Oi, Adv. Immunol. 44:65 (1988) (which preserves the ligand-binding properties, but which also retains the immunogenicity of the nonhuman variable domains); (b) by grafting only the nonhuman CDRs onto human framework and constant regions with or without retention of critical framework residues (Jones et al. Nature, 321:522 (1986); Verhoeyen et al., Science 239:1539 (1988)); or (c) by transplanting the entire nonhuman variable domains (to preserve ligand-binding properties) but also "cloaking" them with a human-like surface through judicious replacement of exposed residues (to reduce antigenicity) (Padlan, Molec. Immunol. 28:489 (1991)).

Humanization by CDR grafting typically involves transplanting only the CDRs onto human fragment onto human framework and constant regions. Theoretically, this should substantially eliminate immunogenicity (except if allotypic or idiotypic differences exist). However, it has been reported that some framework residues of the original antibody also need to be preserved (Riechmann et al., Nature 332:323 (1988); Queen et al., Proc. Natl. Acad. Sci. USA 86:10, 029 (1989)). The framework residues which need to be preserved can be identified by computer modeling. Alternatively, critical framework residues may potentially be identified by comparing known antibody combining site structures (Padlan, Molec. Immun. 31(3):169-217 (1994)). The invention also includes partially humanized antibodies, in which the 6 CDRs of the heavy and light chains and a limited number of structural amino acids of the murine monoclonal antibody are grafted by recombinant technology to the CDR-depleted human IgG scaffold (Jones et al., Nature 321:522-525 (1986)).

Deimmunized antibodies are made by replacing immunogenic epitopes in the murine variable domains with benign amino acid sequences, resulting in a deimmunized variable domain. The deimmunized variable domains are linked genetically to human IgG constant domains to yield a deimmunized antibody (Biovation, Aberdeen, Scotland).

The anti-CD3 antibody can also be a single chain antibody. A single-chain antibody (scFV) can be engineered (see, for example, Colcher et al., Ann. N. Y. Acad. Sci. 880:263-80 (1999); and Reiter, Clin. Cancer Res. 2:245-52 (1996)). The single chain antibody can be dimerized or multimerized to generate multivalent antibodies having specificities for different epitopes of the same target CD3 protein. In some embodiments, the antibody is monovalent, e.g., as described in Abbs et al., Ther. Immunol. 1(6):325-31 (1994), incorporated herein by reference.

Pharmaceutical Compositions

The anti-CD3 antibodies described herein can be incorporated into a pharmaceutical composition suitable for oral or mucosal administration, e.g., by ingestion, inhalation, or absorption, e.g., via nasal, intranasal, pulmonary, buccal, sublingual, rectal, or vaginal administration. Such compositions can include an inert diluent or an edible carrier. For the purpose of oral therapeutic administration, the active compound (e.g., an anti-CD3 antibody) can be incorporated with excipients and used in solid or liquid (including gel) form. Oral anti-CD3 antibody compositions can also be prepared using an excipient. Pharmaceutically compatible binding agents, and/or adjuvant materials can be included as part of the composition. Oral dosage forms comprising anti-CD3 antibody are provided, wherein the dosage forms, upon oral administration, provide a therapeutically effective blood level of anti-CD3 antibody to a subject. Also provided are mucosal dosage forms comprising anti-CD3 antibody wherein the dosage forms, upon mucosal administration, provide a therapeutically effective blood level of anti-CD3 antibody to a subject. For the purpose of mucosal therapeutic administration, the active compound (e.g., an anti-CD3 antibody) can be incorporated with excipients or carriers suitable for administration by inhalation or absorption, e.g., via nasal sprays or drops, or rectal or vaginal suppositories.

Solid oral dosage forms include, but are not limited to, tablets (e.g., chewable tablets), capsules, caplets, powders, pellets, granules, powder in a sachet, enteric coated tablets, enteric coated beads, and enteric coated soft gel capsules. Also included are multi-layered tablets, wherein different layers can contain different drugs. Solid dosage forms also include powders, pellets and granules that are encapsulated. The powders, pellets, and granules can be coated, e.g., with a suitable polymer or a conventional coating material to achieve, for example, greater stability in the gastrointestinal tract, or to achieve a desired rate of release. In addition, a capsule comprising the powder, pellets or granules can be further coated. A tablet or caplet can be scored to facilitate division for ease in adjusting dosage as needed. The dosage forms of the present invention can be unit dosage forms wherein the dosage form is intended to deliver one therapeutic dose per administration, e.g., one tablet is equal to one dose. Such dosage forms can be prepared by methods of pharmacy well known to those skilled in the art (see Remington's Pharmaceutical Sciences, 18th ed., Mack Publishing, Easton Pa. (1990)).

Typical oral dosage forms can be prepared by combining the active ingredients in an intimate admixture with at least one excipient according to conventional pharmaceutical compounding techniques. Excipients can take a wide variety of forms depending on the form of preparation desired for administration. For example, excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents. Examples of excipients suitable for use in oral liquid dosage forms include, but are not limited to, water, glycols, oils, alcohols, flavoring agents, preservatives, and coloring agents.

Tablets and capsules represent convenient pharmaceutical compositions and oral dosage forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

As one example, a tablet can be prepared by compression or by molding. Compressed tablets can be prepared, e.g., by compressing, in a suitable machine, the active ingredients (e.g., an anti-CD3 antibody) in a free-flowing form such as powder or granules, optionally mixed with an excipient. Molded tablets can be made, e.g., by molding, in a suitable machine, a mixture of the powdered anti-CD3 antibody compound moistened, e.g., with an inert liquid diluent.

Excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gum tragacanth or gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidinones, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL® PH-101, AVICEL® PH-103 AVICEL® RC-581, AVICEL® PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL® RC-581. Suitable anhydrous or low moisture excipients or additives include AVICEL® PH-103 and Starch 1500® LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pregelatinized starch, and mixtures thereof. The binder or filler in pharmaceutical compositions and dosage forms of the invention is typically present in from about 50 to about 99 weight percent of the pharmaceutical composition or dosage form.

Disintegrants can be used in the pharmaceutical compositions and oral or mucosal dosage forms of the invention to provide tablets that disintegrate when exposed to an aqueous environment. Tablets containing too much disintegrant might disintegrate in storage, while those containing too little might not disintegrate at a desired rate or under desired conditions. Thus, a sufficient amount of disintegrant that is neither too much nor too little to detrimentally alter the release of the active ingredients should be used to form the pharmaceutical compositions and solid oral dosage forms described herein. The amount of disintegrant used varies based upon the type of formulation, and is readily discernible to those of ordinary skill in the art. Typically, pharmaceutical compositions and dosage forms comprise from about 0.5 to about 15 weight percent of disintegrant, preferably from about 1 to about 5 weight percent of disintegrant.

Disintegrants that can be used in pharmaceutical compositions and oral or mucosal dosage forms of the invention include, but are not limited to, agar-agar, alginic acid, calcium carbonate, Primogel, microcrystalline cellulose, croscarmellose sodium, crospovidone, polacrilin potassium, sodium starch glycolate, corn, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate or Sterotes, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Plano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated. A glidant such as colloidal silicon dioxide can also be used.

The pharmaceutical compositions and oral or mucosal dosage forms can further comprise one or more compounds that reduce the rate by which an active ingredient will decompose. Thus the oral dosage forms described herein can be processed into an immediate release or a sustained release dosage form. Immediate release dosage forms may release the anti-CD3 antibody in a fairly short time, for example, within a few minutes to within a few hours. Sustained release dosage forms may release the anti-CD3 antibody over a period of several hours, for example, up to 24 hours or longer, if desired. In either case, the delivery can be controlled to be substantially at a certain predetermined rate over the period of delivery. In some embodiments, the solid oral dosage forms can be coated with a polymeric or other known coating material(s) to achieve, for example, greater stability on the shelf or in the gastrointestinal tract, or to achieve control over drug release. Such coating techniques and materials used therein are well-known in the art. Such compounds, which are referred to herein as "stabilizers," include, but are not limited to, antioxidants such as ascorbic acid and salt buffers. For example, cellulose acetate phthalate, polyvinyl acetate phthalate, hydroxypropylmethyl cellulose phthalate, methacrylic acid-methacrylic acid ester copolymers, cellulose acetate trimellitate, carboxymethylethyl cellulose, and hydroxypropylmethyl cellulose acetate succinate, among others, can be used to achieve enteric coating. Mixtures of waxes, shellac, zein, ethyl cellulose, acrylic resins, cellulose acetate, silicone elastomers can be used to achieve sustained release coating. See, for example, Remington, supra, Chapter 93, for other types of coatings, techniques and equipment.

Liquids for oral or mucosal administration represent another convenient dosage form, in which case a solvent can be employed. In some embodiments, the solvent is a buffered liquid such as phosphate buffered saline (PBS). Liquid oral dosage forms can be prepared by combining the active ingredient in a suitable solvent to form a solution, suspension, syrup, or elixir of the active ingredient in the liquid. The solutions, suspensions, syrups, and elixirs may optionally comprise other additives including, but not limited to, glycerin, sorbitol, propylene glycol, sugars or other sweeteners, flavoring agents, and stabilizers. Flavoring agents can include, but are not limited to peppermint, methyl salicylate, or orange flavoring. Sweeteners can include sugars, aspartame, saccharin, sodium cyclamate and xylitol.

In order to reduce the degree of inactivation of orally administered anti-CD3 antibody in the stomach of the treated subject, an antiacid can be administered simultaneously with the immunoglobulin, which neutralizes the otherwise acidic character of the gut. Thus in some embodiments, the anti-CD3 antibody is administered orally with an antacid, e.g., aluminum hydroxide or magnesium hydroxide such as MAALOX® antacid or MYLANTA® antacid, or an H2 blocker, such as cimetidine or ranitidine. One of skill in the art will appreciate that the dose of antiacid administered in conjunction with an anti-CD3 antibody depends on the particular antacid used. When the antacid is MYLANTA® antacid in liquid form, between 15 ml and 30 ml can be administered, e.g., about 15 ml. When the cimetidine H2 blocker is used, between about 400 and 800 mg per day can be used.

The kits described herein can include an oral anti-CD3 antibody composition as an already prepared liquid oral dosage form ready for administration or, alternatively, can include an anti-CD3 antibody composition as a solid pharmaceutical composition that can be reconstituted with a solvent to provide a liquid oral dosage form. When the kit includes an anti-CD3 antibody composition as a solid pharmaceutical composition that can be reconstituted with a solvent to provide a liquid dosage form (e.g., for oral or nasal administration), the kit may optionally include a reconstituting solvent. In this case, the constituting or reconstituting solvent is combined with the active ingredient to provide a liquid oral dosage form of the active ingredient. Typically, the active ingredient is soluble in the solvent and forms a solution. The solvent can be, e.g., water, a non-aqueous liquid, or a combination of a non-aqueous component and an aqueous component. Suitable non-aqueous components include, but are not limited to oils; alcohols, such as ethanol; glycerin; and glycols, such as polyethylene glycol and propylene glycol. In some embodiments, the solvent is phosphate buffered saline (PBS).

For administration by inhalation, the mucosal anti-CD3 antibody compounds can be delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal means. For transmucosal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal drops or sprays, or rectal or vaginal suppositories.

The anti-CD3 antibody compounds can also be prepared in the form of suppositories (e.g., with conventional suppository bases such as cocoa butter and other glycerides) or retention enemas for rectal delivery.

In one embodiment, the oral or mucosal anti-CD3 antibody compositions are prepared with carriers that will protect the anti-CD3 antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of such anti-CD3 antibody compositions can be determined by standard pharmaceutical procedures in cell cultures (e.g., of cells taken from an animal after mucosal administration of an anti-CD3 antibody) or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions which exhibit high therapeutic indices are preferred. While anti-CD3 antibody compositions that exhibit toxic side effects may be used, care should be taken to design a delivery system that targets such compounds to the site of affected tissue in order to minimize potential damage and, thereby, reduce side effects.

The data obtained from the cell cultures (e.g., of cells taken from an animal after mucosal administration of an anti-CD3 antibody) and animal studies can be used in formulating a range of dosage for use in humans. The dosage of anti-CD3 antibody compositions lies preferably within a range of circulating concentrations that include the $ED_{50}$ with little or no toxicity. The dosage may vary within this range depending upon the dosage form employed and the route of administration utilized. For any oral or mucosal anti-CD3 antibody compositions used in the methods described herein, the therapeutically effective dose can be estimated initially from assays of cell cultures (e.g., of cells taken from an animal after mucosal administration of an anti-CD3 antibody). A dose may be formulated in animal models to achieve a desired circulating plasma concentration of IL-10 or TGF-β, or of regulatory cells, in the range that includes the $IC_{50}$ (i.e., the concentration of the test compound which achieves a half-maximal inhibition of symptoms) as determined in cell culture. Such information can be used to more accurately determine useful doses in humans. Levels of IL-10 or TGF-β in plasma can be measured by methods known in the art, for example, by ELISA. Levels of regulatory cells can be measured by methods known in the art, for example, by flow cytometry-based methods.

As defined herein, a therapeutically effective amount of an anti-CD3 antibody (i.e., an effective dosage) depends on the antibody selected, the mode of delivery, and the condition to be treated. For instance, single dose amounts in the range of approximately 1 μg/kg to 1000 μg/kg may be administered; in some embodiments, about 5, 10, 50, 100, or 500 μg/kg may be administered. In some embodiments, e.g., pediatric subjects, about 1 to 100 μg/kg, e.g., about 25 or 50 μg/kg, of anti-CD3 antibody can be administered. The anti-CD3 antibody compositions can be administered from one or more times per day to one or more times per week; including once every other day. The oral or mucosal anti-CD3 antibody compositions can be administered, e.g., for about 10 to 14 days or longer. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds can include a single treatment or, can include a series of treatments.

The oral or mucosal anti-CD3 antibody compositions can also include one or more therapeutic agents useful for treating an autoimmune disorder. Such therapeutic agents can include, e.g., NSAIDs (including COX-2 inhibitors); other antibodies, e.g., anti-cytokine antibodies, e.g., antibodies to IFN-α, IFN-γ, and/or TNF-α; gold-containing compounds; immunosuppressive drugs (such as corticosteroids, e.g., prednisolone and methyl prednisolone; cyclophosphamide; azathioprine; mycophenolate mofetil (MMF); cyclosporin and tacrolimus; methotrexate; or cotrimoxazole); heat shock proteins (e.g., as described in U.S. Pat. No. 6,007,821); and treatments for MS, e.g., β-interferons (e.g., interferon β-1a, interferon β-1b), mitoxantrone, or glatiramer acetate.

The pharmaceutical compositions can be included in a container, pack, or dispenser together with instructions for administration.

Methods of Treatment and Prevention

The oral and mucosal anti-CD3 antibody compositions described herein can be administered to a subject to treat or prevent disorders associated with an abnormal or unwanted immune response, e.g., an autoimmune disorder, e.g., by affecting the functional properties of the circulating CD3+ T cells (e.g., reducing their proliferative capacity) or by inducing regulatory cells. Examples of autoimmune disorders include, but are not limited to, Alopecia Areata, Lupus, Ankylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjögren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The oral anti-CD3 antibody compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

In some embodiments, a therapeutically effective amount of an oral or mucosal anti-CD3 antibody composition can be, e.g., the amount necessary to reduce T cell proliferation by about at least 20%. In some embodiments, T cell proliferation is reduced by at least about 30%, about 40%, about 50%, about 60%, about 70% about 80%, or about 90% from pre-treatment levels. In addition, concentrations of IL-10 and/or TGF-β, or levels of cells secreting these cytokines, can be measured in the peripheral blood, e.g., using an enzyme-linked immunosorbent assay (ELISA) or a cell-based assay such as FACS scanning, to monitor the induction of tolerance. In some embodiments, a therapeutically effective amount of an oral or mucosal anti-CD3 antibody composition is the amount necessary increase levels of cells secreting IL-10 and/or TGF-β as measured in the peripheral blood by about 20% or more. In some embodiments, levels of cells secreting IL-10 and/or TGF-β as measured in the peripheral blood are increased by at least about 60%, 70%, 80%, 90%, or 100%, e.g., doubled.

The methods of treatment or prevention typically include administering to a subject an oral or mucosal anti-CD-3 antibody composition sufficient to stimulate the mucosal immune system. In some embodiments, the methods include administering an oral or mucosal anti-CD3 antibody composition sufficient to increase IL-10 and/or TGF-β production by T cells in the peripheral blood, e.g., regulatory T cells, e.g., by about 100%, 200%, 300% or more. In some embodiments, the methods include administering an oral anti-CD3 antibody composition sufficient to decrease T cell proliferation in the peripheral blood, e.g., by about 20%; e.g., in some embodiments, by at least about 20%, 30%, 40%, 50%, 60%, 70%, 80%, 90%, or more. In some embodiments, the methods include administering an oral or mucosal anti-CD3 antibody composition sufficient to increase serum concentrations of IL-10 and/or TGF-β, e.g., measured using an enzyme-linked immunosorbent assay (ELISA), to monitor the induction of tolerance. In some embodiments, the methods include administering an oral or mucosal anti-CD3 antibody composition sufficient to increase levels of regulatory cells in the serum. In some embodiments, the methods include administering an oral or mucosal anti-CD3 composition sufficient to produce an improvement in one or more clinical markers of disability; for example, in multiple sclerosis, such markers could include gadolinium-enhancing lesions visualized by MRI, or Paty's, Fazekas' or Barkhof's MRI criteria, or McDonald's diagnostic criteria; in diabetes, such markers could include blood or plasma glucose levels, glucosuria, ketonuria, polyuria, polydipsia, weight loss with normal or even increased food intake, fatigue, and blurred vision.

Cytokine Release Syndrome (CRS) is not expected to be associated with orally administered anti-CD3 antibodies, but the methods can include monitoring the subjects for signs and symptoms of Cytokine Release Syndrome, particularly after the first few doses but also after a treatment hiatus with resumption of therapy; such methods are particularly useful in determining the safety of oral or mucosal administration of the anti-CD3 antibodies. CRS is associated with arthralgias, myalgias, fevers, chills, hypoxia, nausea, and vomiting; severe cytokine release syndrome can cause pulmonary edema and suffocation. In some embodiments, the methods include lowering the subject's temperature to less than about 37.8° C. (100° F.) before the administration of any dose of the anti-CD3 antibody compositions. In some embodiments, the methods include screening the subject for clinical evidence of volume overload, uncontrolled hypertension, or uncompensated heart failure. In some embodiments, the methods include not administering the oral or mucosal anti-CD3 antibodies to subjects who have evidence of any of, volume overload, uncontrolled hypertension, or uncompensated heart failure. In some embodiments, the methods involve evaluating the subject's pulmonary function, and not administering the anti-CD3 antibodies to subjects who do not have a clear chest X-ray. In some embodiments, the methods include monitoring CD3+ T cell clearance and/or plasma levels of anti-CD3 antibody, and adjusting the dosage of the oral or mucosal anti-CD3 compositions accordingly.

In some embodiments, the methods include administering to the subject methylprednisolone sodium succinate 8.0 mg/kg, e.g., intravenously, e.g., 1 to 4 hours before administration of the oral or mucosal anti-CD3 antibody compositions. In some embodiments, the methods can include administering to the subject an anti-inflammatory agent, e.g., acetaminophen or antihistamine, before, concomitantly with, or after administration of the oral or mucosal anti-CD3 compositions.

In some embodiments, the methods include evaluating and/or monitoring a subject for anti-mouse antibodies, and discontinuing administration of the oral or mucosal anti-CD3 antibody compositions if the subject has anti-mouse antibody titers of greater than about 1:1000. The development of anti-mouse antibodies is not expected with orally or mucosally administered anti-CD3 antibodies.

In some embodiments, the oral or mucosal anti-CD3 antibody compositions are administered concurrently with one or more second therapeutic modalities, e.g., symptomatic treatment, high dose immunosuppressive therapy and/or autologous peripheral blood stem cell transplantation (HSCT). Such methods are known in the art and can include administration of agents useful for treating an autoimmune disorder, e.g., NSAIDs (including selective COX-2 inhibitors); other antibodies, e.g., anti-cytokine antibodies, e.g., antibodies to IFN-α, IFN-γ, and/or TNF-α; gold-containing compounds; heat shock proteins (e.g., as described in U.S. Pat. No. 6,007, 821); immunosuppressive drugs (such as corticosteroids, e.g., prednisolone and methyl prednisolone; cyclophosphamide; azathioprine; mycophenolate mofetil (MMF); cyclosporin and tacrolimus; methotrexate; or cotrimoxazole) and therapeutic cell preparations, e.g., subject-specific cell therapy, hematopoietic stem cell therapy. In some embodiments, the methods include administering one or more treatments for multiple sclerosis, e.g., β-interferons (e.g., interferon β-1a, interferon β-1b), mitoxantrone, or glatiramer acetate. In some embodiments, the methods include administering one or more non-anti-CD3 immunosuppressive drugs (such as corticosteroids, e.g., prednisolone and methyl prednisolone; cyclophosphamide; azathioprine; mycophenolate mofetil (MMF); cyclosporin and tacrolimus; methotrexate; or cotrimoxazole) to the subject, e.g., before, during, or after administration of the oral or mucosal anti-CD3 compositions.

In some embodiments, the methods include administering one or more standard treatments for diabetes, e.g., administration of one or more agents useful in the treatment of diabetes, e.g., insulin, sulfonylureas (e.g., meglitinides and nateglinides), biguanides, thiazolidinediones, and alpha-glucosidase inhibitors, inter alia, as well as modification of diet or exercise regime.

Treatment or Prevention of Multiple Sclerosis

Multiple Sclerosis (MS) is typically characterized clinically by recurrent or chronically progressive neurologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease.

Thus, the invention includes methods of treating, delaying or preventing the onset of MS, by orally or mucosally administering an anti-CD3 antibody.

Included are methods wherein a subject who has or is at risk of having MS is orally administered anti-CD3 antibody. In one aspect, the invention features methods of screening for subjects at risk for MS, e.g., by screening for one or more indicators of MS to evaluate if the subject is at risk for developing MS, and orally or mucosally administering anti-CD3 antibody if the subject is determined to be at risk. As susceptibility to MS is at least partly familial, subjects who have a relative with MS can be considered at increased risk for developing MS.

In some embodiments, the methods include orally or mucosally administering a therapeutically effective amount of anti-CD3 antibody to a subject diagnosed with MS. The diagnosis of MS is typically made on the basis of the clinical signs and symptoms, include heat sensitivity, internuclear ophthalmoplegia, optic neuritis, and Lhermitte symptom (see, e.g., McDonald et al., Recommended Diagnostic Criteria for Multiple Sclerosis: Guidelines From the International Panel on the Diagnosis of Multiple Sclerosis. Ann. Neurol. 50:121, 2001). A therapeutically effective amount can be an amount sufficient to prevent the onset of an acute episode or to shorten the duration of an acute episode, or to decrease the severity of one or more symptoms, e.g., heat sensitivity, internuclears ophthalmoplegia, optic neuritis, and Lhermitte symptom. In some embodiments, a therapeutically effective amount is an amount sufficient to prevent the appearance of or promote the healing of a demyelinated lesion in one or more of the brain, optic nerves, and spinal cord of the subject, e.g., as demonstrated on MRI.

In some embodiments, the oral or mucosal anti-CD3 antibody is administered in combination with a standard treatment for MS, e.g., administration of corticosteroid therapy, interferon beta-1b, Glatiramer, mitoxantrone, cannabis, or a combination thereof. In some embodiments, the oral anti-CD3 antibody is administered in combination with a treatment for one or more symptoms of MS, e.g., depression and fatigue, bladder dysfunction, spasticity, pain, ataxia, and intention tremor; such treatments include pharmacological agents, exercise, and appropriate orthotics. Additional information on the diagnosis and treatment of MS can be found at the National MS Society website, on the world wide web at nationalmssociety.org, the contents of which are incorporated by reference herein.

The median time from onset of disease to disability severe enough for the subject to require aids for ambulation is about 15 years; thus, in some embodiments the invention includes a method of delaying the onset of disability due to MS comprising administering a therapeutically effective amount of an oral anti-CD3 antibody.

Treatment of Prevention of Diabetes Mellitus

There is strong evidence for a cell-mediated autoimmune process being involved in the destruction of beta cells in the majority of cases of type 1 diabetes mellitus. Thus, the methods described herein include methods of treating or preventing diabetes mellitus, e.g., Type I (also sometimes referred to as insulin-dependent or juvenile-onset) diabetes.

Included are methods wherein a subject who has or is at risk of having diabetes mellitus is orally or mucosally administered anti-CD3 antibody. In one aspect, the invention features methods of preventing diabetes by screening for subjects at risk for diabetes, e.g., by screening for elevated or otherwise abnormal blood glucose levels to evaluate if the subject is at risk for developing diabetes, and administering oral anti-CD3 antibody if the subject is determined to be at risk. Subjects at risk for diabetes include subjects with a familial history of type I diabetes, as offspring and siblings of subjects with type 1 diabetes mellitus are at increased risk for the disease. Others who may be considered at risk for diabetes include younger individuals if they are obese (>120% desirable body weight or a body mass index=27), have a first-degree relative with diabetes, are members of a high-risk ethnic population (African American, Hispanic American, Native American, Asian American), have delivered a baby weighing more than 9 lb, have previously had gestational diabetes mellitus (GDM; permanent diabetes will develop in approximately 50% of subjects within 10 years of GDM), are hypertensive (blood pressure=140/90 mm Hg), have atherogenic dyslipidemia (high-density lipoprotein [HDL] cholesterol levels=35 mg/dl or triglyceride levels=250 mg/dl) or had impaired glucose tolerance (IGT) or impaired fasting glucose (IFG) on previous testing. Individuals having or at risk of developing diabetes caused by chronic pancreatitis, pancreatectomy, or carcinoma of the pancreas can also be treated using the methods described herein.

A subject who has been determined to be at risk for diabetes can then be treated prophylactically with oral or mucosal administration of an anti-CD3 antibody to prevent or delay the development of diabetes, or reduce the severity of the diabetes, e.g., reduce the subject's dependence on injected insulin; other measures can be used concurrently to help prevent diabetes, e.g., modification in diet or exercise, administration of oral anti-diabetics, or other methods known in the art.

The invention also includes methods of treating a subject having diabetes, comprising orally or mucosally administering a therapeutically effective amount of an anti-CD3 antibody. A diagnosis of type 1 diabetes mellitus can be made, e.g., on the basis of symptom history confirmed by a blood or plasma glucose level greater than 200 mg/dl, with the presence of glucosuria and/or ketonuria. The classic symptoms of diabetes are polyuria, polydipsia, weight loss with normal or even increased food intake, fatigue, and blurred vision, commonly present 4 to 12 weeks before the symptoms are noticed. Before clinical onset of type 1 diabetes mellitus, diagnosis may be possible with serologic methods, e.g., complemented by beta cell function tests.

A therapeutically effective amount of an orally or mucosally administered anti-CD3 antibody can be an amount sufficient to produce one or more of the following: (1) decreasing plasma glucose levels and urine glucose excretion to eliminate polyuria, polydipsia, polyphagia, caloric loss, and adverse effects such as blurred vision from lens swelling and susceptibility to infection, particularly vaginitis in women, (2) abolishing ketosis, (3) inducing positive nitrogen balance to restore lean body mass and physical capability and to maintain normal growth, development, and life functioning, (4) preventing or greatly minimizing the late complications of diabetes, i.e., retinopathy with potential loss of vision, nephropathy leading to end stage renal disease (ESRD), and neuropathy with risk of foot ulcers, amputation, Charcot joints, sexual dysfunction, potentially disabling dysfunction of the stomach, bowel, and bladder, atherosclerotic cardiovascular, peripheral vascular, and cerebrovascular disease. The current American Diabetes Association standards of care include (1) maintaining preprandial capillary whole blood glucose levels at 80 to 120 mg/dl, bedtime blood glucose levels at 100 to 140 mg/dl, and postprandial peak blood glucose levels at less than 180 mg/dl, and (2) maintaining an HbA1c of less than 7.0% (relative to a nondiabetic DCCT range of approximately 4.0% to 6.0%).

The oral or mucosal anti-CD3 antibody can administered alone or in combination with a standard diabetes therapy, e.g., including but not limited to the administration of one or more agents useful in the treatment of diabetes, e.g., insulin, sulfonylureas (e.g., meglitinides and nateglinides), biguanides, thiazolidinediones, and alpha-glucosidase inhibitors, inter alia, as well as modification of diet or exercise regime. Additional information about the diagnosis and treatment of diabetes can be found in the chapter on Diabetes Mellitus on the Scientific American Medicine/WebMD website on the world wide web at samed.com, the contents of which are incorporated herein by reference.

Treatment of Autoimmune Arthritis

Rheumatoid arthritis (RA) is the most common chronic inflammatory arthritis and affects about 1% of adults; it is two to three times more prevalent in women than in men. RA may begin as early as infancy, but onset typically occurs in the fifth or sixth decade. Diagnosis may be made according to the American Rheumatism Association Criteria for the Classification of Rheumatoid Arthritis. A therapeutically effective amount will cause an improvement in one or more of the following: the number of inflamed joints, the extent of swelling, and the range of joint motion. Laboratory measurements (e.g., ESR and hematocrit value) and assessments of subjective features (e.g., pain and morning stiffness) can also be made. The invention includes methods of treating autoimmune arthritis, e.g., RA, in a subject by administering to the subject a therapeutically effective amount of an anti-CD3 antibody.

In some embodiments, the methods include the administration of a second therapeutic agent, e.g., for analgesia, to additionally control inflammation, and/or to alter the natural history of the disease. A number of such agents are known in the art. For example, one or more of NSAIDs, methotrexate, prednisone, TNF inhibitors, leflunomide, or sulfasalazine (with or without hydroxychloroquine) can be administered. Immunosuppressive agents such as azathioprine or cyclosporine can also be used.

Treatment or Prevention of Allograft Rejection

The methods described herein can also be used to treat or prevent graft rejection in a transplant recipient. For example, the methods can be used in a wide variety of tissue and organ transplant procedures, e.g., the methods can be used to induce central tolerance in a recipient of a graft of cells, e.g., stem cells such as bone marrow and/or of a tissue or organ such as pancreatic islets, liver, kidney, heart, lung, skin, muscle, neuronal tissue, stomach, and intestines. Thus, the new methods can be applied in treatments of diseases or conditions that entail cell, tissue or organ transplantation (e.g., liver transplantation to treat hypercholesterolemia, transplantation of muscle cells to treat muscular dystrophy, or transplantation of neuronal tissue to treat Huntington's disease or Parkinson's disease). In some embodiments, the methods include administering to a subject in need of treatment: 1) an anti-CD3 antibody, and 2) a donor organ or tissue, e.g., liver, kidney, heart, lung, skin, muscle, neuronal tissue, stomach and intestines.

In some embodiments, the transplanted tissue comprises pancreatic islets. Accordingly, the invention encompasses a method for treating diabetes by pancreatic islet cell transplantation. The method comprises administering to a subject in need of treatment: 1) an anti-CD3 antibody; and 2) donor pancreatic islet cells. Typically, the anti-CD3 antibody is administered to the recipient prior to and/or simultaneously with administration of the pancreatic islets.

In some embodiments, the recipient is then treated with a regimen of immune-suppressing drugs to prevent rejection of the tissue or organ. Standard regimens of immunosuppressive treatment are known. Tolerance to donor antigen can be evaluated by standard methods, e.g., by MLR assays.

In some embodiments, the donor is a living, viable human being, e.g., a volunteer donor, e.g., a relative of the recipient. In some embodiments, the donor is no longer living, or is brain dead, e.g., has no brain stem activity. In some embodiments, the donor tissue or organ is cryopreserved. In some embodiments, the donor is one or more non-human mammals, e.g., an inbred or transgenic pig, or a non-human primate.

EXAMPLES

The invention is further described in the following examples, which do not limit the scope of the invention described in the claims.

Materials and Methods

Anti-CD3 Antibodies

Hybridoma cells producing the hamster 145-2C11 mAb (IgG anti-mouse CD3ε-chain) were purchased from ATCC. The hybridoma cells were grown in an Integra flask in DMEM medium containing 10% Low Ig FCS; 10% NCTC-109; 1% non-essential amino acids; 1% sodium pyruvate; 1% L-glutamine; 1% antibiotic/antimycotic; 0.2% gentamycin. Flasks were split twice a week and supernatants were collected and sent to Strategic Biosolutions (Newark, Del.) to concentration and purification.

Purified Hamster IgG (ICN Pharmaceuticals, Inc.) was used as an isotype control (IC).

Feeding Anti-CD3 Antibody: SJL Mouse Model

Female SJL mice (a strain that exhibits experimental autoimmune encephalomyelitis (EAE) following immunization with myelin proteolipid protein (PLP)), at age 8 weeks were fed with anti-CD3 antibody (5, 50 and 500 μg/mouse) in PBS for 5 consecutive days by gavage using an 18-gauge stainless feeding needle. Spleens and mesenteric lymph nodes (MLN) were removed from the mice, typically 24-48 hours after the last feeding.

Two-Color Flow Cytometry

Two-color flow cytometry was performed as follows. $1 \times 10^6$ cells isolated from spleens and MLN removed 24 hours after the last feeding were incubated in staining buffer (PBS with 4% BSA and 0.1% sodium azide) for 5 min. The cells were then stained with phycoerythrin (PE)-labeled anti-mouse CD25 and fluorescein isothiocyanate (FITC) labeled anti-mouse CD4 for 30 min. The cells were washed twice and then fixed in PBS with 1% formaldehyde. The analysis was performed on FACScan flow cytometer with CellQuest software.

Proliferation of Spleen and MLN Cells

T cells from fed and non-fed mice were isolated from spleens and mesenteric lymph nodes (MLN) using mouse CD90 (Thy1.2) MACS MicroBeads. $1 \times 10^5$ T cells were cultured 1:1 with irradiated spleen cells from non-fed mice and stimulated with 0.5 μg/ml anti-CD3 in DMEM supplemented with 10% heat-inactivated FBS, 2 mM L-glutamine, 100 U/ml penicillin, 100 μg/ml streptomycin, and 50 μM 2-ME. Cultures were pulsed with [$^3$H] Thymidine (1 μCi/well) 72 hours later and harvested 16 h later.

Induction and Evaluation of Clinical Course of EAE, an Animal Model of MS, in PLP-Immunized Mice Two days after the last feeding with the anti-CD3 antibodies, experimental allergic encephalomyelitis (EAE, an animal model of multiple sclerosis) was induced in the SJL mice by immunization in the footpad with a fragment of myelin proteolipid protein (PLP) (139-151) 50 μg/mouse emulsified 1:1 in complete Freunds adjuvant (CFA). Pertussis toxin (PT) 150 ng was given i.v. at the time of immunization and 48 hours later. EAE was scored as follows: 0, no disease; 1, limp tail; 2, hind limb weakness; 3, hind limb paralysis; 4, hind and forelimb paralysis; 5, moribund.

Cytokine Assay

Spleen cells were harvested 41 days after immunization as described above. Cells were isolated and red blood cells were removed by lysis. Splenocytes were cultured at $1 \times 10^6$ cells/well in 250 μl of Ex-Vivo 20 serum-free medium with or without PLP antigen. Supernatants were collected after 40 hours for IL-10 and 72 hours for TGF-β. The levels of cytokines in the supernatants were determined by standard capture ELISA. Briefly, microtiter plates were coated with rat anti-mouse IL-10 mAb at 1 μg/ml in 0.1 M carbonate buffer pH 8.2 at 4° C. overnight. Plates were washed and blocked for 2 hours at room temperature (RT) with 10% BSA solution. Standards and supernatant samples were added and incubated overnight at 4° C. Plates were washed and biotinylated rat anti-mouse IL-10 mAb added for 1 hour at RT, followed by washing, and incubation for 30 minutes at RT with peroxidase-labeled streptavidin.

For TGF-β quantification, plates were coated with 5 μg/ml polyclonal chicken anti-TGF-β for overnight incubation at 4° C. Mouse monoclonal anti-TGF-β was used as secondary antibody. Peroxidase-labeled goat anti-mouse IgG was used for detection. Bound cytokine was detected by the addition of 2,2'-azino-bis-(3-ethylbenzothiazoline-6-sulfonic acid) acid (ABTS) and reading at OD 450 nm after color development.

Proliferation Assay: Splenocytes from PLP-Immunized Mice

Splenocytes were cultured at $5 \times 10^5$ cells/well with or without PLP (139-151), for 72 hours. [$^3$H] Thymidine (1 μCi/well) was added for the last 12 hours of culture. Cells were then harvested and incorporation of Thymidine was measured using an LKB Betaplate liquid scintillation counter.

Clinical Course of EAE, an Animal Model of MS, in PLP-Immunized NOD Mice

NOD female mice (a mouse model of Type I diabetes) at age of 8 weeks fed with anti-CD3 antibody (0.5, 5 and 50 μg/mouse) in PBS for 5 consecutive days. Two days after the last feeding, mice were immunized in the footpad with PLP (48-70) 100 μg/mouse emulsified 1:1 in CFA. Pertussis toxin (PT) 150 ng was given i.v. at the time of immunization and 48 hours later. EAE was scored as described above. Spleen cells were harvested 10 days after immunization. Spleen and MLN cells were isolated and cytokine and proliferation assays were performed as described above, with or without stimulation in vitro with PLP 48-70 (1, 10 and 100 μg/ml).

OVA TCR Tg Mice

OVA TCR Tg mice on the BALB/c background, clone DO11.10, were also used; DO11.10 mice, and CD4+ T cells derived from them, express a transgenic T cell receptor (TCR) specific for a 17-amino acid peptide (323-339) derived from ovalbumin (OVA). OVA Tg mice at 8 weeks of age were fed for 5 consecutive days with Isotype control or anti-CD3 antibody (0.5, 5, or 50 μg; or, in some experiments, 50, 200 and 500 μg/mouse) in PBS. Twenty-four hours after the last feeding, spleens and lymph nodes were removed from the mice. Cytokines and proliferation assays were performed as described above, with or without stimulation in vitro with OVA (10,100 and 1000 μg/ml).

Example 1

Clinical Course of EAE in SJL Mice

The study described in this example examined the effect of orally administered anti-CD3 antibody on the clinical course of experimental autoimmune encephalomyelitis (EAE) in SJL mice, a strain of mice susceptible to EAE.

Briefly, SJL mice were fed 5, 50 or 500 μg anti-CD3 antibody for 5 days. Forty-eight hours after the last anti-CD3 antibody feeding, EAE was induced by immunizing the mice with 50 μg PLP (139-151) emulsified with CFA. EAE was scored as follows: 0, no disease; 1, limp tail; 2, hind limb weakness; 3, hind limb paralysis; 4, hind and forelimb paralysis; 5, moribund. The results are shown in FIG. 1. Interestingly, a reverse dose-response was seen, with the best protection resulting from feeding 5 μg of anti-CD3 antibody.

Feeding with 5 μg anti-CD3 antibody delayed the onset, and reduced the severity, of the symptoms of EAE by six days as compared to control (day 13±4, post immunization, in the control group compared with day 19±1.6 in the 5 μg fed group; p=0.04) and decreased maximal disease score from 2.95±0.6 in the control group to 1.1±0.5 in the fed group (p=0.001). On day 24 post immunization, all the animals in the 5 μg fed group fully recovered, while in the control, unfed group the average disease score was 2.65±0.22 (p<0.001). No significant differences in the onset of disease or the maximal disease score were found in the groups fed 50 μg or 500 μg anti-CD3 antibody as compared to the control group. However, the mice that were fed with 50 μg anti-CD3 reached the peak of the disease on day 14, and then started to recover. On day 31, the average disease score in this group was 0.3±0.27 as compared to 2.2±0.7 in the control group (p<0.001).

These results demonstrate that feeding with low doses of oral anti-CD3 antibody can delay and reverse the induction of EAE.

Example 2

Proliferation of Spleen Cells from SJL Mice Immunized with PLP

Proliferation of T cells can be used as a good indicator of the activity of immune regulatory mechanisms; decreased proliferation in response to stimulation has been linked to antigen tolerance and increased levels of anergic, regulatory cells, which can suppress proliferation of other, inflammatory T cells. The study described in this example examined the effect of orally administered anti-CD3 antibody on the on the proliferation of spleen cells following induction of EAE in SJL mice.

Figure 2:
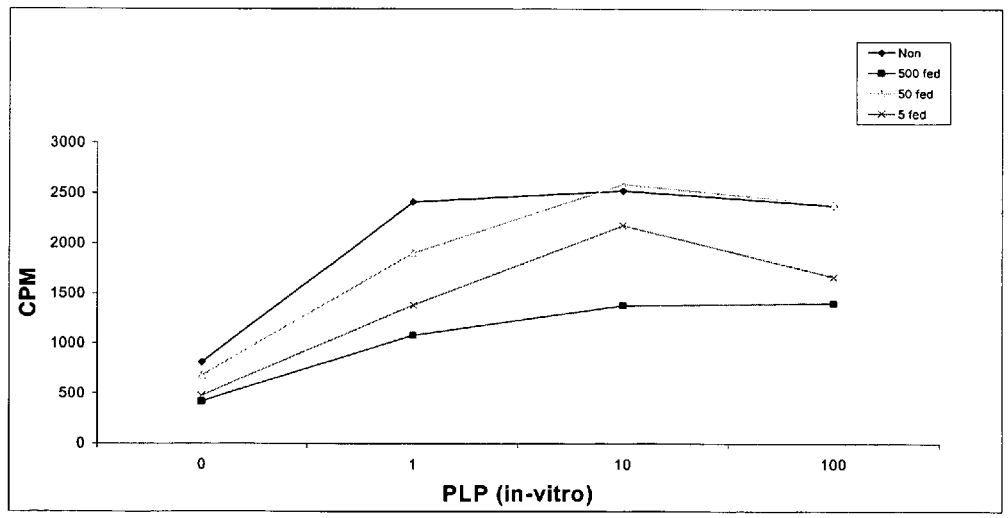
FIG. 2 is a line graph illustrating proliferation of spleen cells isolated from SJL mice fed 5, 50, or 500 µg anti-CD3 antibody and immunized with PLP peptide (139-151) in response to stimulation with the PLP peptide.

SJL mice were fed 5, 50 or 500 μg anti-CD3 antibody for 5 days as described above. 48 hours after the last feeding, mice were immunized with PLP (139-151) 50 μg emulsified with CFA. On day 41 after immunization, spleen cells were prepared and stimulated in vitro with 1, 10 or 100 μg/ml PLP for 72 hours. [$^3$H] thymidine (1 μCi/well) was added for the last 12 h of culture. Cells were then harvested as described above and incorporation of thymidine was measured. Results are shown in FIG. 2; splenocytes isolated from mice fed 500 μg of anti-CD3 antibody showed the least proliferation in response to immunization with PLP; those splenocytes from mice fed 5 μg proliferated more, but less than those from mice fed 50 μg, which proliferated similarly to unfed mice, illustrating a unique dose-responsiveness for this phenomenon.

The effects seen at the 5 μg dose were confirmed in additional experiments. Briefly, SJL mice were fed 5 μg anti-CD3 antibody for 5 days. 48 hours after the last feeding mice were immunized with PLP (139-151) 50 μg emulsified with CFA. On day 41 after immunization, spleen cells were prepared and stimulated in vitro with PLP 1, 10 and 100 μg/ml for 72 hours. [$^3$H] Thymidine (1 μCi/well) was added for the last 12 hours of culture. Cells were then harvested and incorporation of thymidine was measured. Results are shown in FIG. 3. Again, a dose of 5 μg anti-CD3 antibody was shown to be effective in reducing splenocyte proliferation in response to challenge with PLP. This result is evidence that the oral administration of anti-CD3 antibodies increases regulation of the immune system, thus decreasing disease-inducing immune response in PLP-immunized SJL mice.

Example 3

CD4+/CD25+ T Cell Response in MLNs Isolated from SJL Mice Immunized with PLP

The study described in this example examined the effect of orally administered anti-CD3 antibody on levels of CD4+/CD25+ T cells, which are thought to participate in the mucosal immune response and may serve to actively suppress antigen-specific responses, and Latency Associated Peptide (LAP)+ cells, associated with the precursor of TGF-β, in mesenteric lymph nodes (MLN), which are associated with the mucosal immune system, in PLP-immunized SJL mice.

Briefly, SJL mice were fed 5 μg/ml anti-CD3 antibody or Isotype control (IC) for 5 days as described above. On day 6, lymphocytes from MLN from 3 mice in each group were pooled, prepared and stained for CD4 and CD25 or LAP, and analyzed by flow cytometry as described above.

The results for the CD4+/CD25+ cells, shown in FIG. 4, are as follows: Non fed: 11.9%; fed IC: 9.83%; fed aCD3-5: 23.76%. Thus, MLNs isolated from mice that were not fed anti-CD3 (non fed), or fed an isotype-matched control (fed IC), had similar levels of CD4+/CD25+ cells (about 10-12%), while MLN from mice fed 5 μg anti-CD3 had increased levels of CD4+/CD25+ cells (about 24%).

In some instances there was an increase of CD4+LAP+ cells in the spleen and MLN after feeding anti-CD3; in the spleen, there was an increase from 5.5% to 7.9%; in the MLN, from 2.0% to 3.2%; and in the Peyer's patches, CD4+LAP+ cells increased from 4% to 5.2%. These results were statistically significant.

These results provide evidence that the decreased immune response associated with the oral administration of anti-CD3 antibodies is associated with increased numbers of CD4+/CD25+ and CD4+LAP+ T cells in the MLN, which demonstrates specific activation of T cells in the MLN after oral administration of anti-CD3.

Example 4

T Cell Proliferation in SJL Mice

The study described in this example examined the effect of orally administered anti-CD3 antibody on T cell proliferation in non-immunized SJL mice.

Figure 5A:
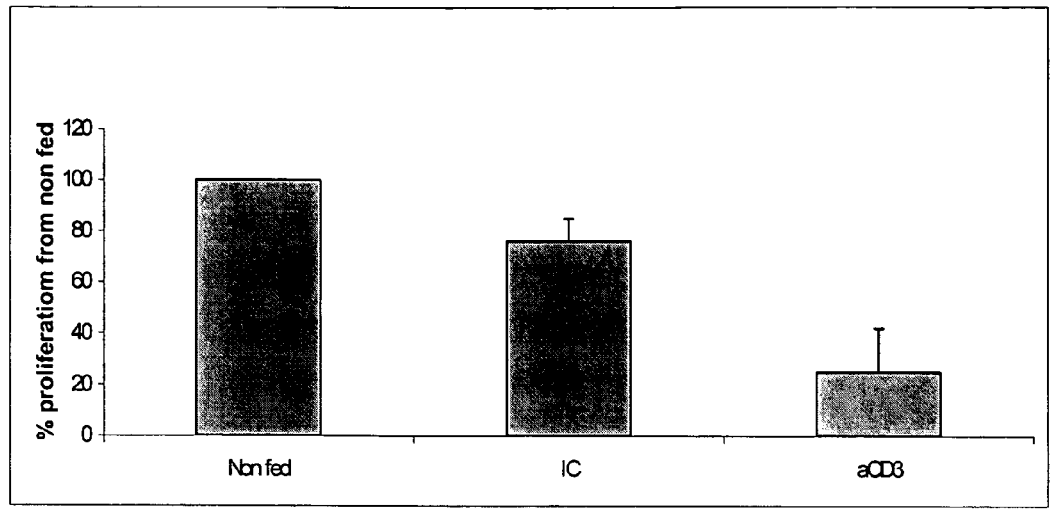
FIGS. 5A and 5B are bar graphs illustrating the proliferation of T cells in spleen (5A) and MLN (5B) isolated from SJL mice fed 5 µg anti-CD3 or isotype-matched control.
Figure 5B:
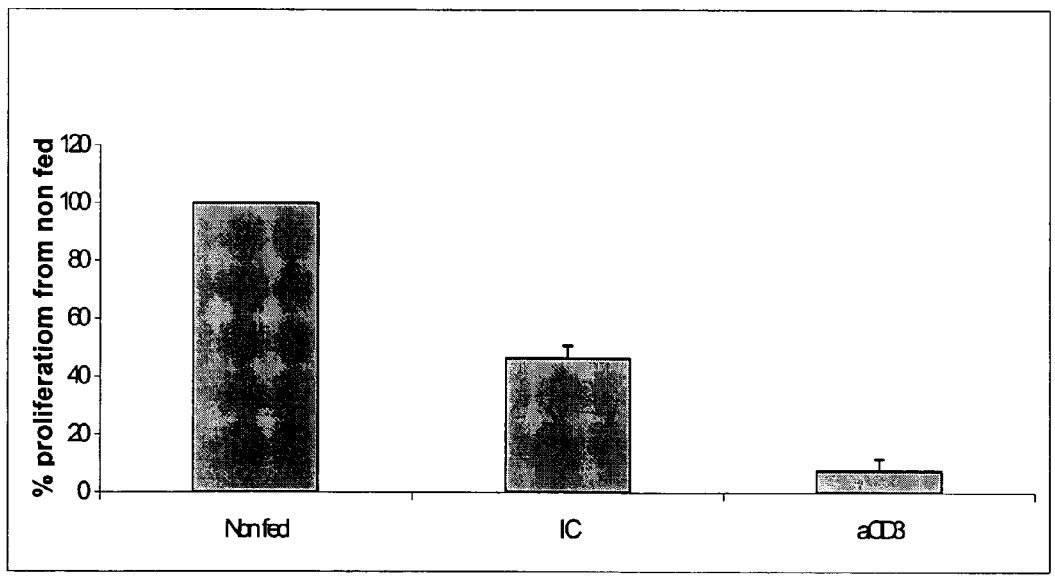

T cells from fed and non-fed SJL mice were isolated from spleen (FIG. 5A) and MLN (5B) using mouse CD90 (Thy1.2) MACS MicroBeads. $1 \times 10^5$ T cells were cultured 1:1 with irradiated spleen cells from non-fed mice and stimulated with 0.5 μg/ml anti-CD3 in DMEM supplemented with 10% heat-inactivated FBS, 2 mM L-glutamine, 100 U/ml penicillin, 100 μg/ml streptomycin, and 50 μM 2-ME. Cultures were pulsed with [$^3$H] thymidine (1 μCi/well) 72 hours later, and harvested 16 hours later. The results, shown in FIGS. 5A and B, indicate that spleen and MLN from mice fed with 5 μg/ml anti-CD3 antibody had reduced T cell proliferation as compared to control. Proliferation of T cells in non-fed mice was set as 100%. Proliferation of T cells isolated from the spleens of mice fed anti-CD3 antibody was 25%±10 versus non-fed controls (p<0.01; FIG. 5A); proliferation of T cells isolated from the MLN of mice fed anti-CD3 antibody was 7.5%±4 versus non-fed controls (p<0.01; FIG. 5B). (Significance determined using the two-tailed student's t test)

These results indicate that the anti-inflammatory activity of orally administered anti-CD3 activity is associated with decreased T cell proliferative responses in the MLN and the spleen of non-immunized SJL mice.

Example 5

Comparison Clinical Course of EAE in NOD Mice

The study described in this example examined the effect of oral administration of low doses of anti-CD3 antibodies on the induction and symptoms of EAE in NOD mice, a model of autoimmune diabetes. NOD mice are susceptible to experimental autoimmune encephalomyelitis (EAE) induced by the proteolipoprotein (PLP) epitope 56-70, and thus provide another animal model of MS.

Figure 6:
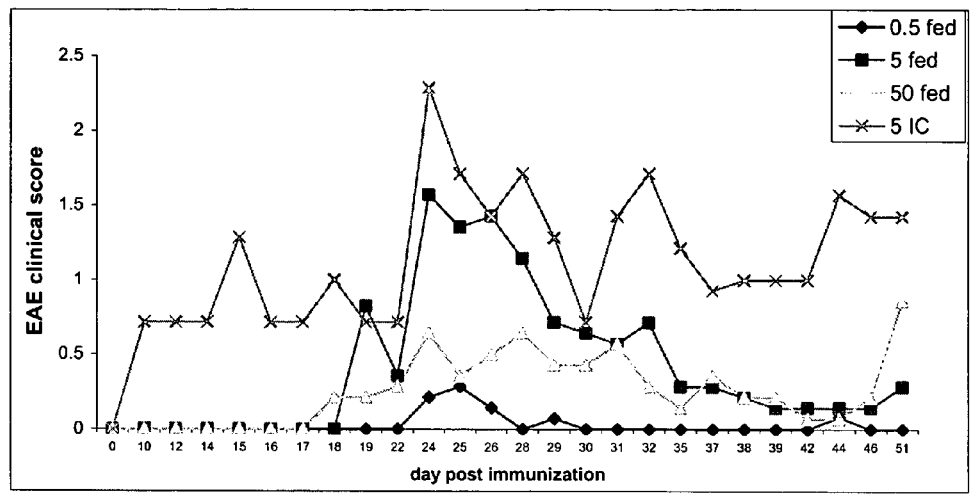
FIG. 6 is a line graph illustrating the course of EAE in PLP peptide (48-70)-immunized NOD mice fed 0.5, 5, or 50 µg anti-CD3 antibody.

Briefly, as described above, the mice were fed 0.5, 5 or 50 μg anti-CD3 antibody or IC for 5 days. 48 hours after the last feeding, mice were immunized with 100 μg PLP (48-70) emulsified with CFA. EAE was scored as follows: 0, no disease; 1, limp tail; 2, hind limb weakness; 3, hind limb paralysis; 4, hind and forelimb paralysis; 5, moribund. The results are shown in FIG. 6. The statistical analysis was performed using mean cumulative score±SEM (Non-fed: 8.7±1.4; fed 0.5 μg: 0.8±0.4; fed 5 μg: 10.9±4.2; fed 50 μg: 6.7±2.9; fed IC: 13.2±5). The results show that in PLP-immunized NOD mice fed with 5 μg anti-CD3, there is a significant inhibition of EAE as compared to the non-fed group (p=0.0006) and to the IC group (p=0.005). Further, the effect of orally administered CD3 is not specific to a single animal model (see Example 1, indicating therapeutic efficacy in SJL mice), strain or peptide, and so is likely to work in humans.

Example 6

Proliferation of Spleen Cells from NOD Mice Immunized with PLP

The study described in this example examined the effect of orally administered anti-CD3 antibody on T cell proliferation in NOD mice immunized with PLP.

Figure 7:
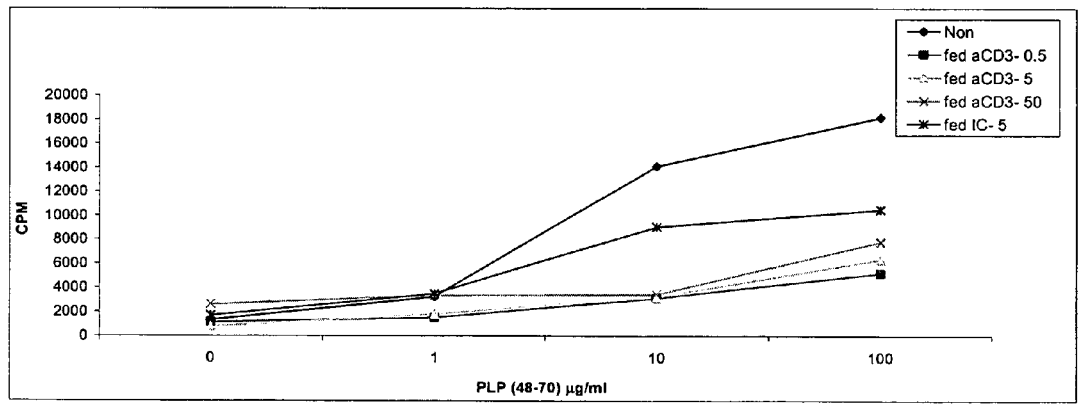
FIG. 7 is a line graph illustrating the proliferation of spleen cells isolated from NOD mice fed 0.5, 5, or 50 µg anti-CD3 antibody, or 5 µg isotype-matched control, and immunized with PLP peptide (48-70), in response to stimulation with the PLP peptide in vitro.
Figure 8:
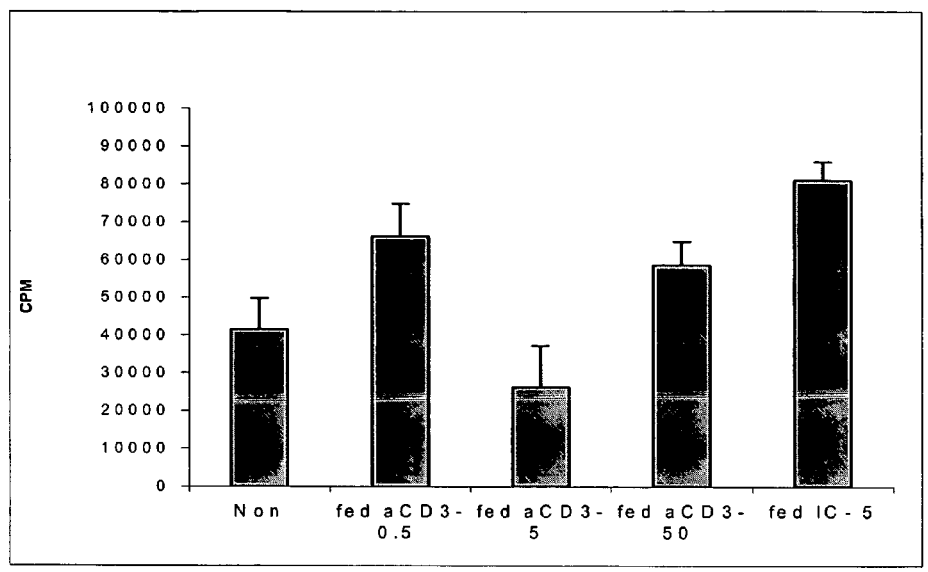
FIG. 8 is a bar graph illustrating the proliferation of spleen cells isolated from NOD mice fed 0.5, 5, or 50 µg anti-CD3 antibody, or 5 µg isotype-matched control, and immunized with PLP peptide (48-70), in response to stimulation with anti-CD3 antibody.

NOD mice were fed 0.5, 5 or 50 μg anti-CD3 antibody or IC for 5 days. Forty-eight hours after the last feeding, mice were immunized with 100 μg PLP (48-70) emulsified with CFA. On day 10 after immunization, spleen cells were prepared and stimulated in vitro with 1, 10 or 100 μg/ml PLP for 72 hours. [$^3$H] thymidine (1 μCi/well) was added for the last 12 hours of culture. Cells were then harvested. The results, shown in FIGS. 7 and 8, demonstrate that oral administration of low doses of anti-CD3 antibody results in decreased T cell proliferation. Proliferation of spleen cells from NOD fed 5 μg anti-CD3 was 26198±696 cpm, which was significantly lower (p<0.01) when compared to mice that were fed with IC (81000±2009 cpm).

This result is evidence that the oral administration of anti-CD3 antibodies decreases disease-inducing immune responses in PLP-immunized NOD mice.

Example 7

Cytokine Production in Spleen Cells from NOD Mice Immunized with PLP

The study described in this example examined the effect of orally administered anti-CD3 antibody on the production of the cytokine IL-10 in spleen cells from NOD mice exhibiting EAE after immunization with PLP.

Figure 9:
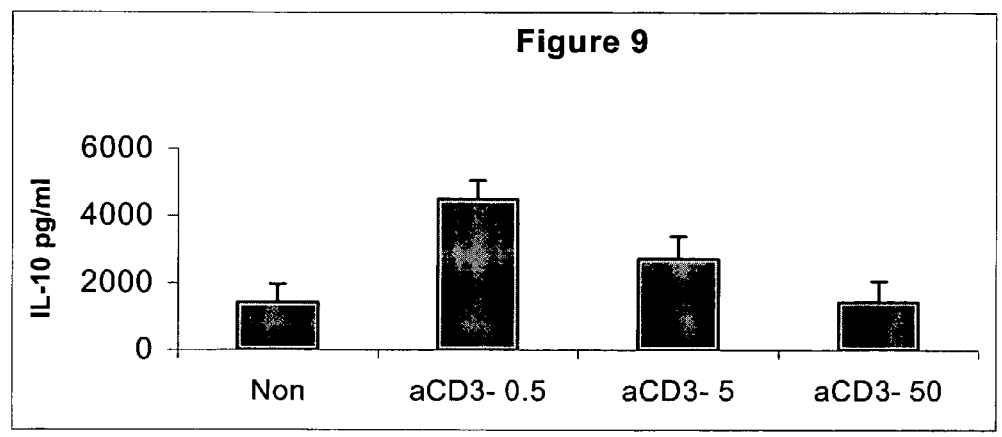
FIG. 9 is a bar graph illustrating the production of IL-10 in spleen cells isolated from NOD mice fed 0.5, 5, or 50 µg anti-CD3 antibody, and immunized with PLP peptide (48-70), in response to stimulation with anti-CD3 antibody.

NOD mice were fed 0.5, 5 or 50 μg anti-CD3 antibody or IC for 5 days. 48 hours after the last feeding, mice were immunized with PLP (48-70) 100 μg emulsified with CFA. On day 10 after immunization, spleen cells were prepared and stimulated in vitro with 1 μg/ml anti-CD3 antibody. Supernatants were collected after 40 hours and IL-10 was measured by ELISA. The results are shown in FIG. 9. Level of IL-10 secreted by the different groups: non-fed: 1422±551; fed 0.5 μg: 4489±566; fed 5 μg: 2726±661; fed 50 μg: 1438±620; fed IC: 3005±764. The level of IL-10 from mice that were fed with 0.5 μg anti-CD3 was significantly higher compared to the non fed mice p=0.01. This illustrates that oral administration of low doses of anti-CD3 antibody results in increased IL-10 production as compared to control. This provides evidence that the therapeutic activity of orally administered anti-CD3 antibody may be mediated at least in part by increased levels of IL-10, which is known as regulatory Th2 cytokine involved in the reversal of EAE.

Example 8

Cytokine Production in Spleen Cells from OVA TCR Transgenic Mice

The study described in this example examined the effect of orally administered anti-CD3 antibody on the production of the anti-inflammatory cytokines IL-10 and TGF-β in spleen cells from ovalbumin (OVA)-specific T-cell receptor transgenic ("OVA TCR Tg" or "OVA Tg") mice.

Figure 10A:
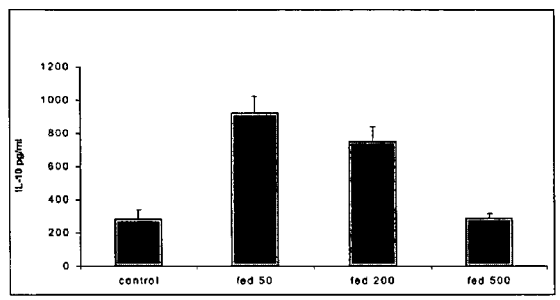
FIGS. 10A and 10B are bar graphs illustrating levels of IL-10 (10A) and TGF-β (10B) secreted by spleen cells isolated from OVA transgenic (Tg) mice fed 50, 200, or 500 µg anti-CD3 antibody, in response to in vitro stimulation with OVA.
Figure 10B:
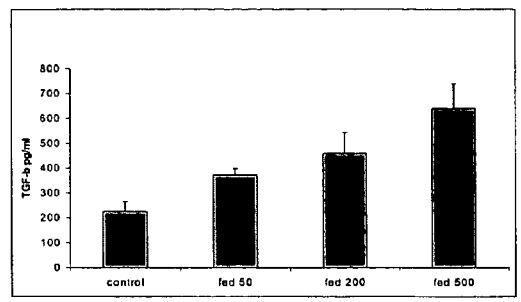

OVA TCR Tg mice were fed 5 consecutive days with isotype control (IC) or anti-CD3 antibody (50, 200, or 500 μg; the higher doses required for effectiveness in these mice may be due to their transgenic nature). Twenty-four hours after the last feeding, spleens were removed from the mice. Spleen cells were prepared and stimulated in vitro with 1000 μg/ml OVA. Supernatants were collected after 40 hours for IL-10 measurements (FIG. 10A) and after 72 hours for TGF-β measurements (FIG. 10B). Cytokine levels were measured by ELISA. The IL-10 results, as shown in FIG. 10A, were as follows (IL-10, μg/ml): control: 283±56; fed 50 μg: 923±99; fed 200 μg: 750±89; fed 500 μg: 289±25. The level of IL-10 fed 50 and 200 was significantly higher (p<0.01; p=0.01, respectively). The levels of TGF-β, as shown in FIG. 10B, were as follows (TGF-β, pg/ml): control 225±40; fed 50 μg: 373±25; fed 200 μg: 460±85; fed 500 μg: 640±100. This illustrates that the level of TGF-β in the mice that were fed 50, 200 and 500 μg of anti-CD3 antibody was significantly higher (p=0.05; p<0.01, p<0.01, respectively). These results demonstrate that oral administration of low doses (50 μg) of anti-CD3 antibody result in increased IL-10 production as compared to control, and higher doses (500 μg) of anti-CD3 antibody result in significantly increased TGF-β production. Thus, the higher doses of orally administered anti-CD3 antibody may be affecting a different population of cells, possibly Th3 cells associated with TGF-β production as opposed to Th2 cells associated with IL-10 production.

Example 9

Proliferation of Spleen Cells from OVA Tg Mice

The study described in this example examined the effect of orally administered anti-CD3 antibody on the proliferation of spleen cells from ovalbumin (OVA)-specific T-cell receptor transgenic ("OVA TCR Tg" or "OVA Tg") mice.

Figure 11:
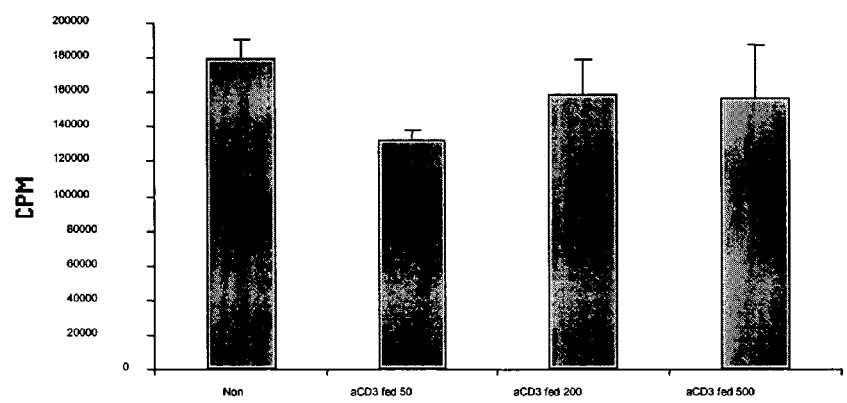
FIG. 11 is a bar graph illustrating the proliferation of spleen cells isolated from OVA Tg mice fed 50, 200, or 500 µg anti-CD3 antibody, in response to stimulation with OVA.

OVA Tg mice were fed for 5 consecutive days with isotype control or anti-CD3 antibody (50, 200, and 500 μg). Twenty-four hours after the last feeding, spleens were removed from the mice. Spleen cells were prepared, and stimulated in vitro with 10, 100 or 1000 μg/ml OVA for 72 hours (control cells were unstimulated). [$^3$H] Thymidine (1 μCi/well) was added for the last 12 hours of culture. Cells were then harvested. The results are shown in FIG. 11. The average proliferation of the different groups, expressed as (CPM)±STDEV, was as follows: non-fed: 180100±1000; fed 50 μg: 133176±5200; fed 200 μg: 158951±20000; fed 500 μg: 157200±30000. The proliferation of cells from mice that were fed 50 μg anti-CD3 antibody was significantly reduced compared to the non-fed group (p<0.05). Thus, in non-immunized (e.g., normal) Tg mice the oral administration of higher doses of anti-CD3 antibody appears to have little effect on spleen cell proliferation.

Example 10

Allogeneic Cardiac Transplantation

The study described in this example examined the effect of oral treatment with anti-CD3 antibody on survival after allogeneic cardiac transplantation.

Briefly, a dose of 5 μg of anti-CD3 antibody (clone 145-2C11) in 200 μl volume was administered to C57BL/6 mice by oral gavage each day beginning on day −5 and continuing until day +10 post transplantation (for a total of 16 administrations); day 0 being the day of transplantation. The mice received heart transplants from BALB/c donor mice, and were monitored for cessation of heartbeat to determine the day of rejection.

Cardiac transplants in control mice receiving no anti-CD3 treatment survived an average of 8.4±1.0 days (n=11); cardiac transplants in mice receiving the anti-CD3 treatment survived an average of 16.2±5.8 days (n=5; p=0.0004 by Logrank test). Thus, oral administration of anti-CD3 antibody can successfully delay or prevent allograft rejection.

Example 11

Chronic Model of EAE

The study described in this example examined the effect of oral administration of low doses of anti-CD3 antibodies on the induction and symptoms of EAE in NOD mice, a model of autoimmune diabetes. Fifteen week old NOD mice, when immunized with the MOG (35-55) peptide, are a model for chronic EAE/MS.

14 week old female NOD mice were fed 0.5, 5 or 50 μg anti-CD3 antibody or IC for 5 days. Forty-eight hours after the last feeding, mice were immunized with the encephalitogenic myelin oligodendrocyte glycoprotein (MOG) (35-55) peptide, 150 μg emulsified with CFA, and EAE was scored as described. The statistical analysis was performed using Mean cumulative score±SEM. As is illustrated in FIG. 12, EAE scores were as follows at day 83: Non-fed: 39±14.58; fed 0.5 μg: 33.78±6.79; fed 5 μg: 8.75±14; fed 50 μg: 38.5±16.8; fed IC: 32.9±20.54. Thus, mice that were fed with 5 μg anti-CD3 antibody show significant inhibition of EAE as compared to the non-fed group (p=0.001). This result indicates that the effect of orally administered is not limited to a specific animal model (consider with Examples 1 and 5). Further, the results of this study indicate that orally administered anti-CD3 antibody has therapeutic value in a chronic model of MS, as well as the relapsing/remitting models as illustrated in Examples 1 and 5, which use different antigenic peptide to induce EAE.

Example 12

Proliferation of Spleen and Popliteal Lymph Node (PLN) Cells

The study described in this example examined the effect of oral administration of low doses of anti-CD3 antibodies on the proliferation of spleen and Popliteal Lymph Node (PLN) cells. The PLNs are located near the legs and stomach, and are considered non-specific lymph nodes.

Figure 13A:
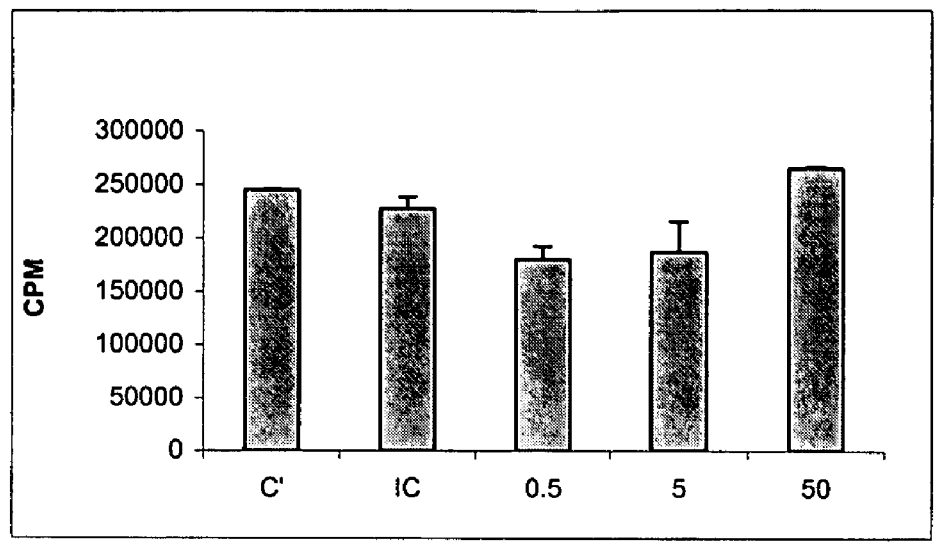
FIG. 13A is a bar graph illustrating the proliferation of spleen cells stimulated in vitro with anti-CD3 2 µg/ml.
Figure 13B:
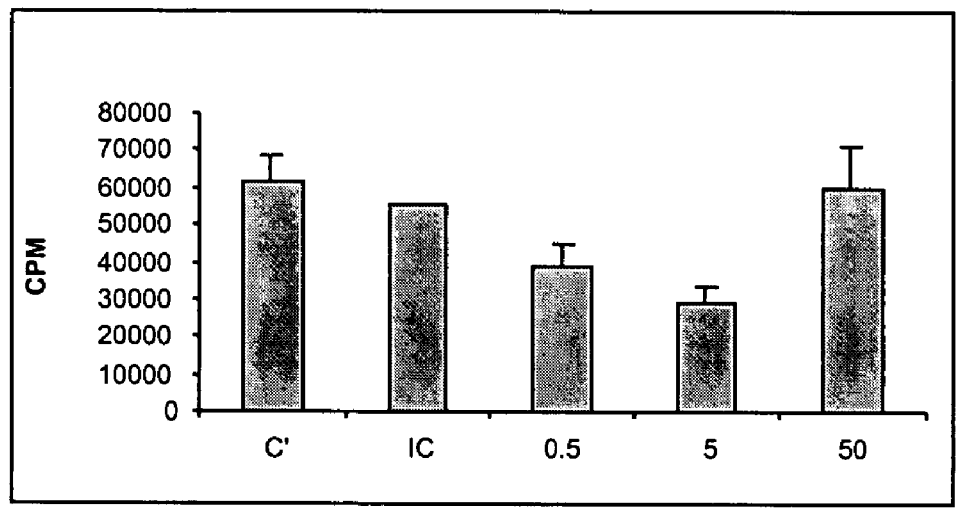
FIG. 13B is a bar graph illustrating the proliferation of PLN cells stimulated with 100 µg/ml PLP.

SJL mice were fed 0.5, 5 or 50 μg anti-CD3 antibody for 5 days. Forty-eight hours after the last feeding, mice were immunized with PLP (139-151) 50 μg emulsified with CFA. On day 10 after immunization, spleen and PLN cells were prepared and stimulated in vitro with anti-CD3 antibody 2 μg/ml (FIG. 13A) and PLP 100 μg/ml (FIG. 13B) respectively, for 72 hours. [$^3$H] Thymidine (1 μCi/well) was added for the last 12 hours of culture. Cells were then harvested and thymidine uptake measured as described.

The proliferation of PLN cells from mice that were fed with 0.5 μg anti-CD3 antibody (38501±6160) and PLN cells from mice that were fed 5 μg anti-CD3 antibody (28900±4578) was significantly reduced as compared to PLN cells from the non fed mice (p=0.03 and p=0.007, respectively). These results indicate that oral administration of anti-CD3 antibody is able to effect a decrease in the inflammatory response outside of, as well as within, the mucosal immune system, as expected for tolerance induced in the gut, which results in systemic tolerance.

Example 13

Cytokine Production in PLN Cells from SJL Mice Immunized with PLP

The study described in this example examined the effect of orally administered anti-CD3 antibody on the production of the cytokine IL-10 in PLN cells from SJL mice exhibiting EAE after immunization with PLP.

Figure 14:
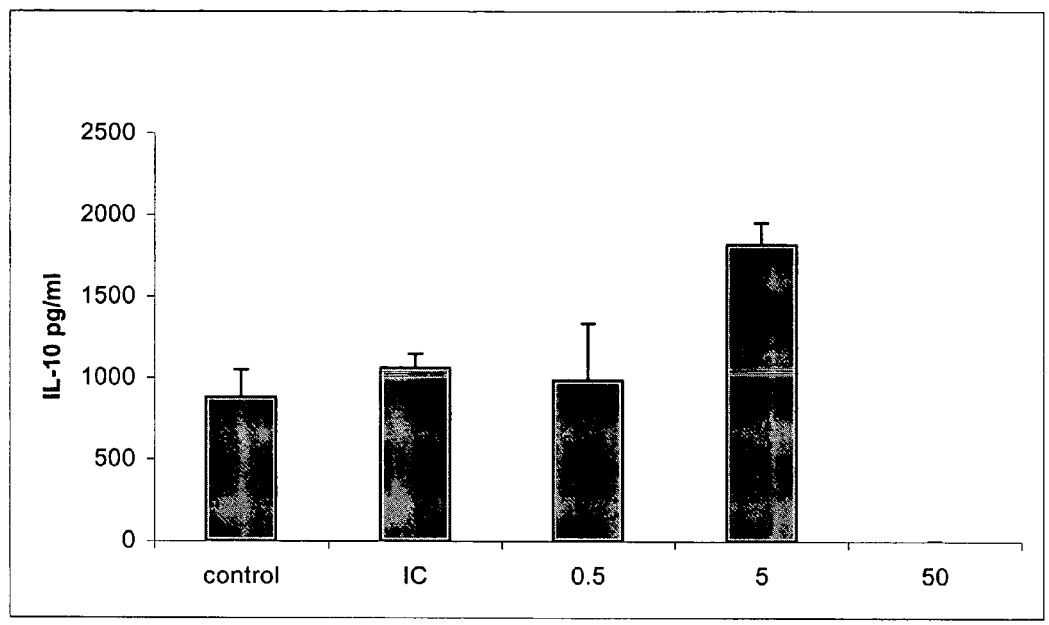
FIG. 14 is a bar graph illustrating the secretion of IL-10 from PLN cells after stimulation with anti-CD3 antibody.

SJL mice were fed 0.5, 5 or 50 μg anti-CD3 antibody or IC for 5 days. Forty-eight hours after the last feeding, mice were immunized with PLP (139-151) 50 μg emulsified with CFA. On day 10 after immunization, PLN cells were prepared and stimulated in vitro with anti-CD3 antibody 1 μg/ml. Supernatant was collected after 40 hours and IL-10 was measured by ELISA. Results are shown in FIG. 14. PLN cells from mice that were fed 5 μg aCD3 secrete more IL-10 after stimulation in vitro with anti-CD3 antibody as compared to the non-fed and the IC groups (p=0.02). This provides further evidence that the therapeutic activity of orally administered anti-CD3 antibody may be mediated at least in part by increased levels of IL-10.

Example 14

Cytokine Production in Spleen Cells from SJL Mice Immunized with PLP

The study described in this example examined the effect of orally administered anti-CD3 antibody on the production of the cytokine IL-10 in spleen cells from SJL mice exhibiting EAE after immunization with PLP.

SJL mice were fed 0.5, 5 or 50 μg anti-CD3 antibody or IC for 5 days. Forty-eight hours after the last feeding, mice were immunized with PLP (139-151) 50 μg emulsified with CFA. On day 10 after immunization, spleen cells were prepared and stimulated in vitro with anti-CD3 antibody 1 μg/ml. Supernatants were collected after 24 and 40 hours (for IL-2 and IL-10 respectively) and cytokine levels were measured by ELISA.

Figure 15A:
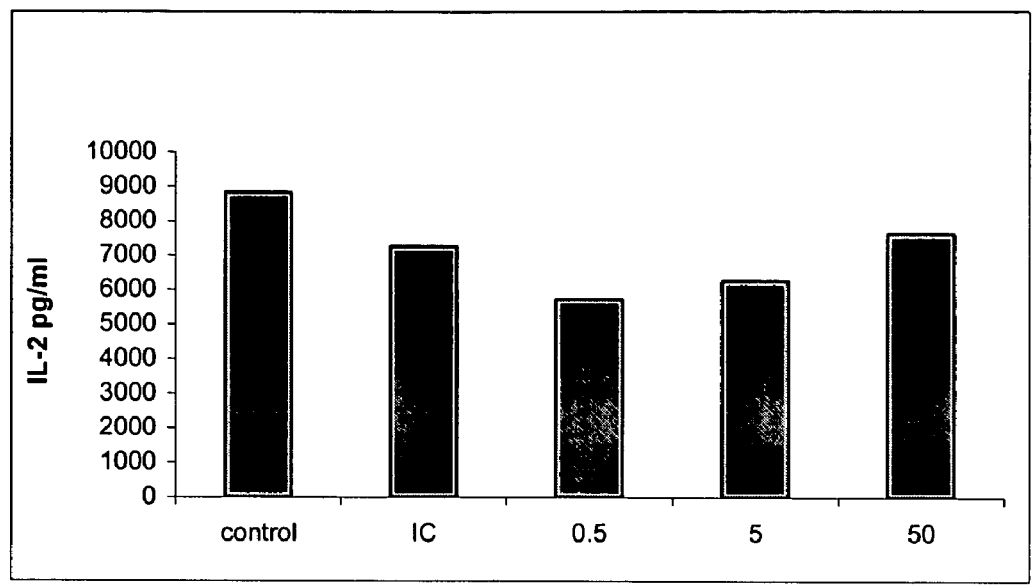
FIGS. 15A and 15B are bar graphs illustrating the secretion of IL-2 (15A) and IL-10 (15B) from spleen cells isolated from mice fed 0.5, 5, or 50 µg anti-CD3 antibody.
Figure 15B:
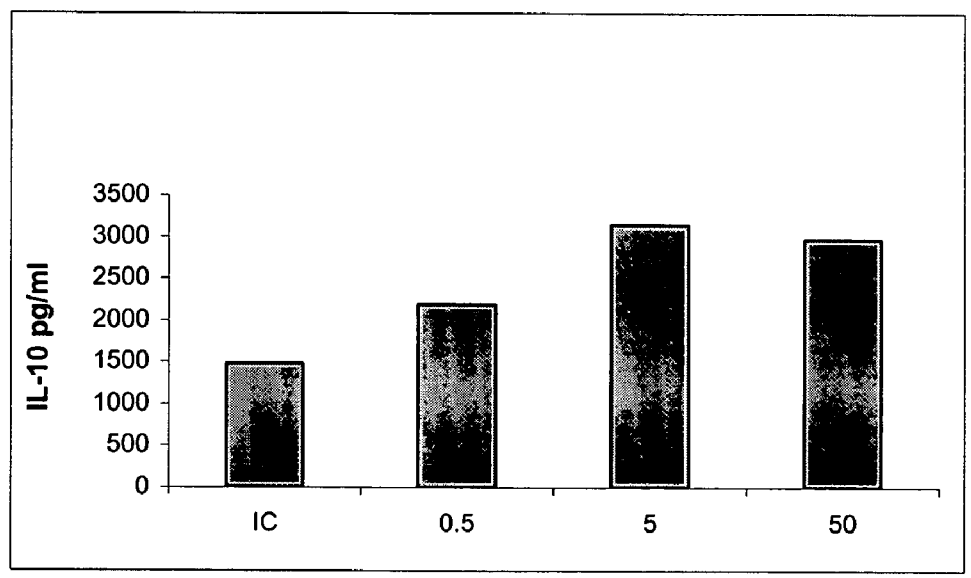
Figure 16A:
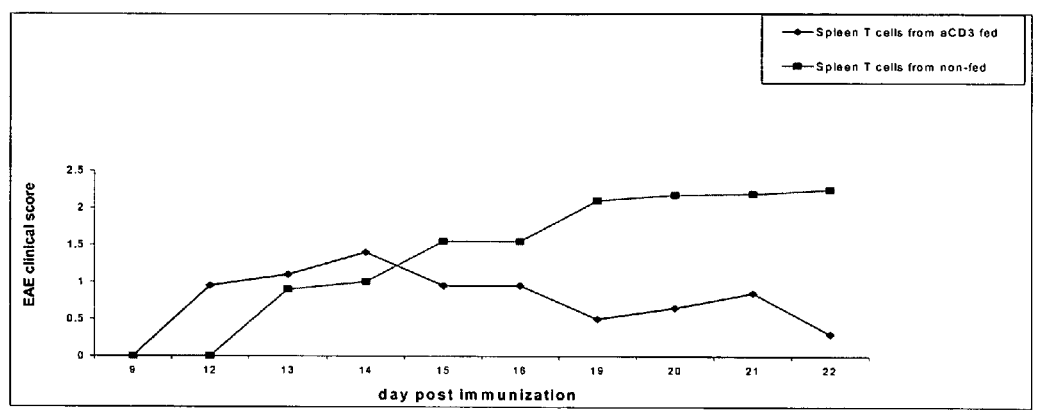
FIGS. 16A and 16B are line graphs illustrating the effect on the clinical course of EAE of injection with cells isolated from the spleen (16A) or MLN (16B) of mice fed with anti-CD3 antibody.
Figure 16B:
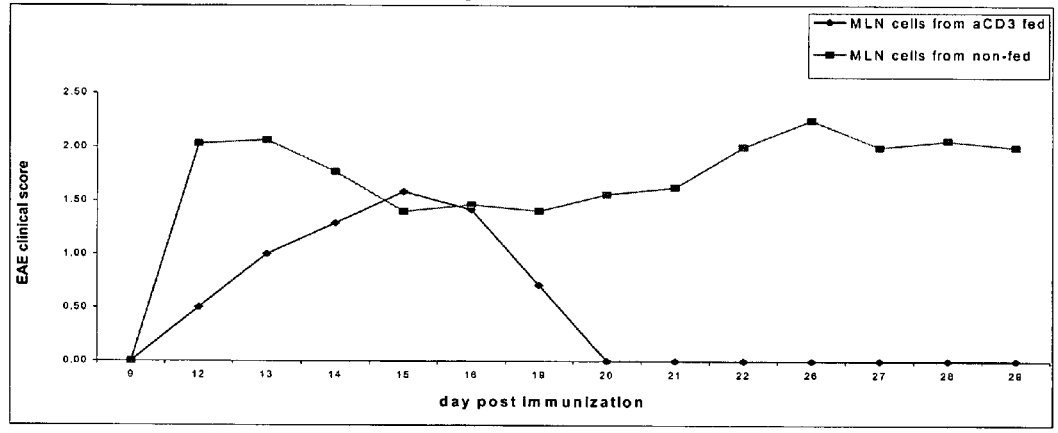

The results demonstrate that cells from fed mice secrete less IL-2 (FIG. 15A) and more IL-10 (FIG. 15B) as compared to IC and non-fed mice. This provides additional evidence that the therapeutic activity of orally administered anti-CD3 antibody is mediated at least in part by increased levels of IL-10; the decreased levels of IL-2 correlate with decreased proliferation and further support the theory that the mechanism involves increased immune regulation and an increased anti-inflammatory response.

Example 15

Adoptive Transfer of Tolerance

The study described in this example examined the effect of injecting recipient mice with T cells isolated from the spleen or mesenteric lymph nodes (MLN) of mice fed with orally administered anti-CD3.

SJL mice were fed 5 μg anti-CD3 antibody for 5 days. Twenty-four hours or seven days after the last feeding T cells were isolated from the spleen or mesenteric lymph nodes (MLN). T cells were purified from the spleen preparation using mouse CD90 MACS MicroBeads. $20 \times 10^6$ T cells from the MLN, or $40 \times 10^6$ T cells from the spleen, were transferred by intravenous infusion to recipient SJL mice, at the same time the mice were immunized with PLP peptide (139-151) as described herein. EAE was scored as described herein.

The results are as follows, expressed as mean cumulative score±STD. MLN from fed mice transferred 24 hours after the last feeding: 4±3.88 (p=0.012); MLN from non-fed mice: 20.1±1.2; spleen T cells from fed mice transferred 1 week after the last feeding: 4.93±3.07 (p=0.027); Spleen T cells from non fed mice: 10.42±2.2. These results demonstrate that oral anti-CD3 antibody induces regulatory T cells that can adoptively transfer protection against EAE in vivo; this protection can be transferred from a mouse fed with anti-CD3 antibody to a naïve recipient mouse.

Example 16

The Effect of Administration of Anti-CD3 Antibody Before or After Induction of EAE The study described in this example examined the effect on the clinical course of EAE of the timing of the oral administration of anti-CD3 antibody, i.e., before and after induction of EAE by immunization of SJL mice with a PLP-derived peptide.

SJL mice were fed 0.5, 5 or 50 µg anti-CD3 antibody or IC for 5 days before immunization (days −7 to −2) and at the peak of the disease (days 13-17 post-immunization). Forty-eight hours after the last feeding, mice were immunized with PLP (139-151) 50 µg emulsified with CFA. EAE was scored as follows: 0, no disease; 1, limp tail; 2, hind limb weakness; 3, hind limb paralysis; 4, hind and forelimb paralysis; 5, moribund. The statistical analysis was performed using Mean cumulative score±SEM.

Figure 17A:
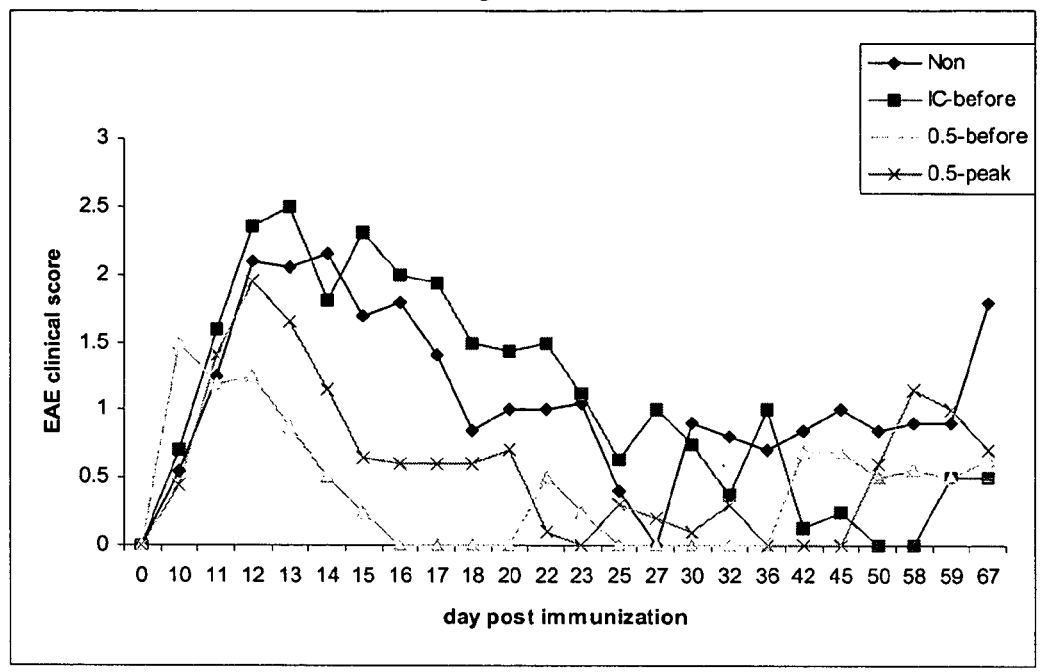
FIGS. 17A, 17B, and 17C are line graphs illustrating the effect on the clinical course of EAE of oral administration of 0.5 µg (17A), 5 µg (17B), or 50 µg (17C) anti-CD3 antibody before induction of EAE or at the peak of disease.
Figure 17B:
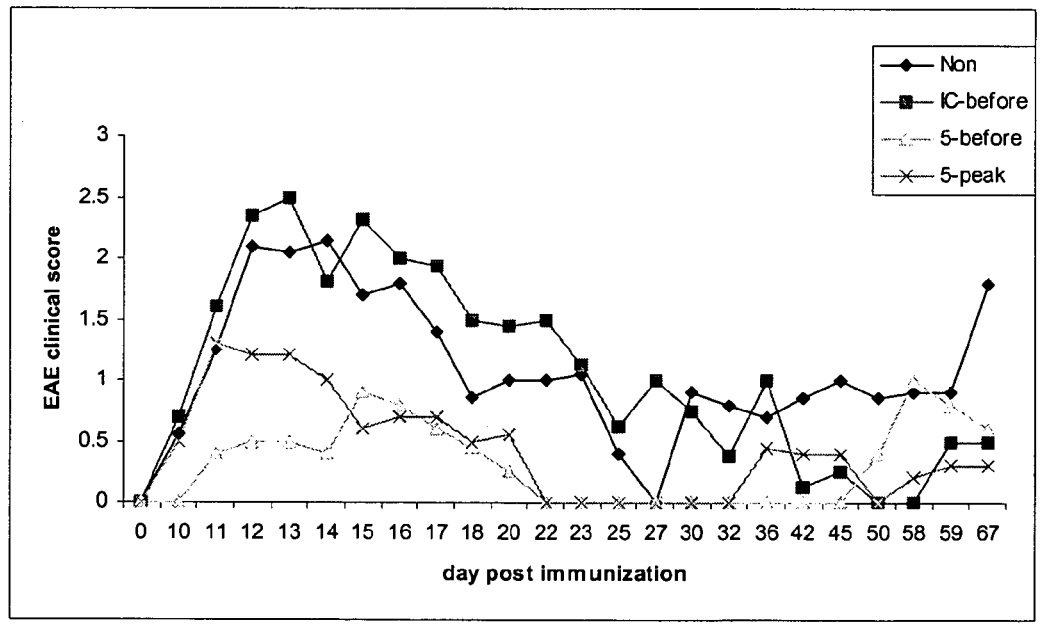
Figure 17C:
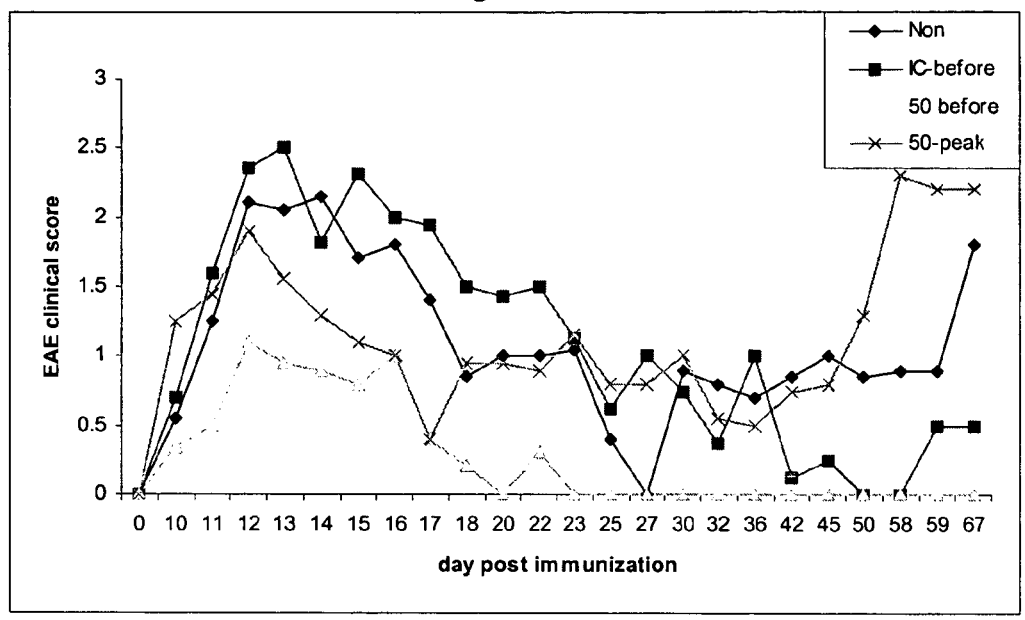

The results are illustrated in FIGS. 17A-C. All the fed mice that were fed before induction of EAE shown significant inhibition of disease as compared to the IC group (fed 0.5 µg anti-CD3 p=0.055; fed 5 µg anti-CD3 p=0.016; fed 50 µg anti-CD3 p=0.03). The mice that were fed with 5 µg anti-CD3 at the peak of the disease (days 13-17) showed significant inhibition of the disease as compared to the group fed IC before immunization with the peptide (days −7 to −2) and at the peak (days 13-17; FIG. 17B; p=0.03; p=0.016 respectively) These results indicate that the administration of oral anti-CD3 antibody after the onset of EAE is also effective at certain doses.

Example 17

The Effect of Oral Administration of Anti-CD3 Antibody on Development of Diabetes The study described in this example examined the effect of feeding newborn NOD mice with 0.5 or 5 µg anti-CD3 antibodies (aCD3), or isotype-matched control (IC) on the subsequent development of spontaneous diabetes.

NOD mice were fed starting 24 hours after birth, as follows:

TABLE 1

NOD mice fed as newborns

| Group (n) | First feeding (5 times, starting 24 h after birth and once a week) | At 3 Weeks of Age (once a week) |
| --- | --- | --- |
| 1 (11) | 0.05 microgram/mouse aCD3 | 0.5 microgram/mouse aCD3 |
| 2 (17) | 0.5 microgram/mouse aCD3 | 5 microgram/mouse aCD3 |
| 3 (11) | 0.05 microgram/mouse IC | 0.5 microgram/mouse IC |

Figure 18:
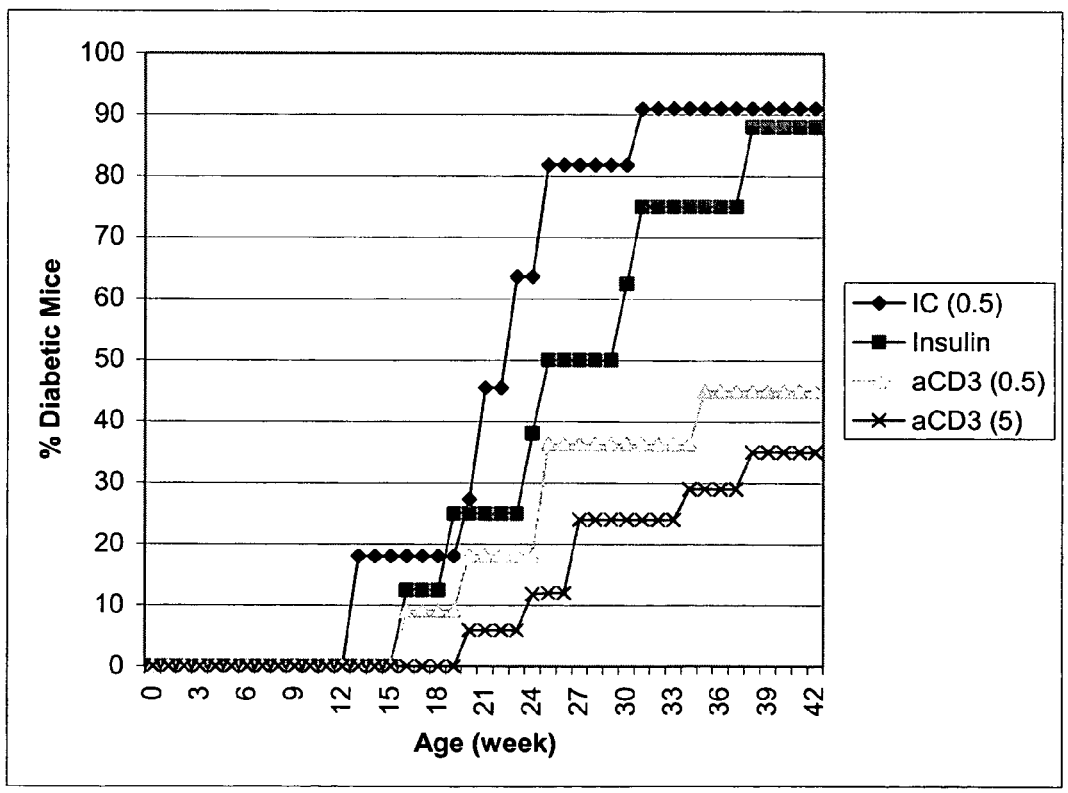
FIG. 18 is a line graph illustrating the effect of oral administration of 0.5 µg (triangles) or 5 µg (circles) anti CD-3 antibody to newborn NOD mice on subsequent development of diabetes, as compared to treatment with insulin (squares) or 0.5 µg of an isotype-matched control (diamonds).

Diabetes was assessed by colorimetric strips to monitor glycosuria. The results of this study, illustrated in FIG. 18, demonstrate that not only did oral administration of anti-CD3 antibody apparently result in delayed onset, the absolute occurrence of diabetes was substantially reduced.

The effect on development of spontaneous diabetes of feeding NOD mice with anti CD3 0.5 µg/feeding or 5 µg/feeding was evaluated at weeks 12 to 33. Both treatments proved to be significantly better than the IC control at preventing the development of diabetes; statistical analysis was performed using the student's t test, with unpaired and two tailed p-value. Oral administration with 0.5 µg anti CD3 has a p-value of 0.0002, and feeding with 5 µg anti CD3 has a p-value of 0.0001 all compared to the IC (0.5) control group.

Example 18

The Effect of Oral and Nasal Administration of Antigen-Binding Fragments of Anti-CD3 Antibody on Clinical Course of EAE The study described in this example examined the effect of orally or nasally administering antigen-binding fragments of anti-CD3 antibodies on the subsequent development of experimental autoimmune encephalomyelitis.

Briefly, female SJL mice that were 6-8 weeks old were either fed 200 µl/mouse every day or nasally administered 10 µl/mouse every other day of F(ab)'2 derived from an anti-CD3 antibody or Isotype-matched Control (IC; hamster IgG), for 5 days, starting a week before induction of EAE. The feeding schedule is shown in Table 2.

TABLE 2

| Feeding Schedule | d-6 | d-5 | d-4 | d-3 | d-2 |
| --- | --- | --- | --- | --- | --- |
| Control PBS | + | + | + | + | + |
| Oral IC; 5 µg | + | + | + | + | + |
| Oral IC; 50 µg | + | + | + | + | + |
| Oral F(ab)'2 αCD3; 5 µg | + | + | + | + | + |
| Oral F(ab)'2 αCD3; 50 µg | + | + | + | + | + |
| Nasal F(ab)'2 αCD3; 0.1 µg | + | | + | | + |
| Nasal F(ab)'2 αCD3; 0.5 µg | + | | + | | + |

EAE was induced by immunizing the mice on day 0 with PLP139-151, 75 µg/mouse; MTb, 400 µg/mouse; Emulsion, 200 µl/mouse; (PBS+Peptide), mixed with an equal volume of Complete Freund's Adjuvant; and Pertissis Toxin (PT), 150 ng/mouse. PT was administered again on day +2, ip.

Figure 19:
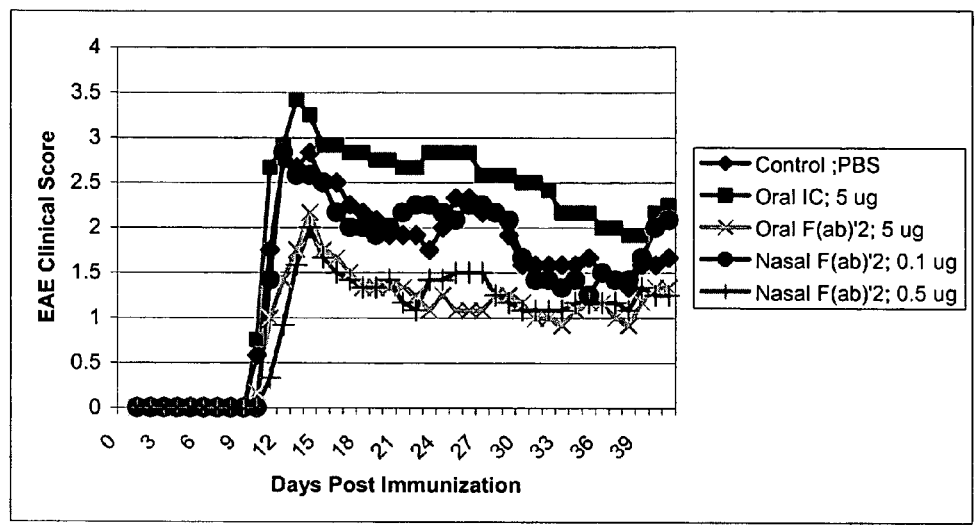
FIG. 19 is a line graph illustrating the effect of oral and nasal administration of an F(ab)'2 fragment on the clinical course of EAE over about 44 days.

The results are shown in FIG. 19, and demonstrate that orally administered (5 µg) and nasally administered (0.5 µg) F(ab')$_2$ both substantially reduced the overall severity and delayed time of onset of EAE. The effects were statistically significant (p<0.05); Oral IC vs. Oral Fab p=0.002; Nasal Fab (0.5) vs. Oral IC=0.005; Nasal Fab (0.5) vs. PBS=0.03; Nasal Fab (0.5) vs. PBS vs. Oral IC p=0.03. These results indicate that orally and nasally administered antigen-binding fragments of the anti-CD3 antibodies are effective in treating EAE, an experimental model of multiple sclerosis.

Example 19

Effect of Orally Administered Anti-CD3 F(ab')$_2$ in Streptozotocin-Induced Model of Diabetes To determine the effect of orally administered anti-CD3 F(ab')$_2$ on diabetes, wild type normal AKR mice (Jackson Laboratory, Bar Harbor, Me.) were treated with streptozotocin (STZ), which has been shown to induce diabetes in these mice. Parenterally administered anti-CD3 antibody has been shown to be effective in these mice, see Herold et al., Diabetes. March 1992; 41(3):385-91.

Briefly, AKR mice 6-8 weeks of age were placed into one of four groups as follows:

Group 1. Non-treated (n=4);

2. Oral PBS+STZ i.p. (40 mg/kg) (n=12), administered once a day for 5 days for 5 total doses;

3. Oral IC (50 μg/0.2 ml/mice)+STZ i.p. (40 mg/kg) (n=12), administered once a day for 5 days for 5 total doses; and
4. Oral Anti-CD3 F(ab')₂ (50 μg/0.2 ml/mice)+STZ i.p. (40 mg/kg) (n=12), administered once a day for 5 days for 5 total doses.

Glucose tolerance tests were administered by measurement of blood glucose at 30 minutes after i.p. injection of 20% glucose/mouse on days 7, 14, 21, and 28. Mice with blood glucose readings>250 mg/dl were diagnosed as diabetes.

Figure 20:
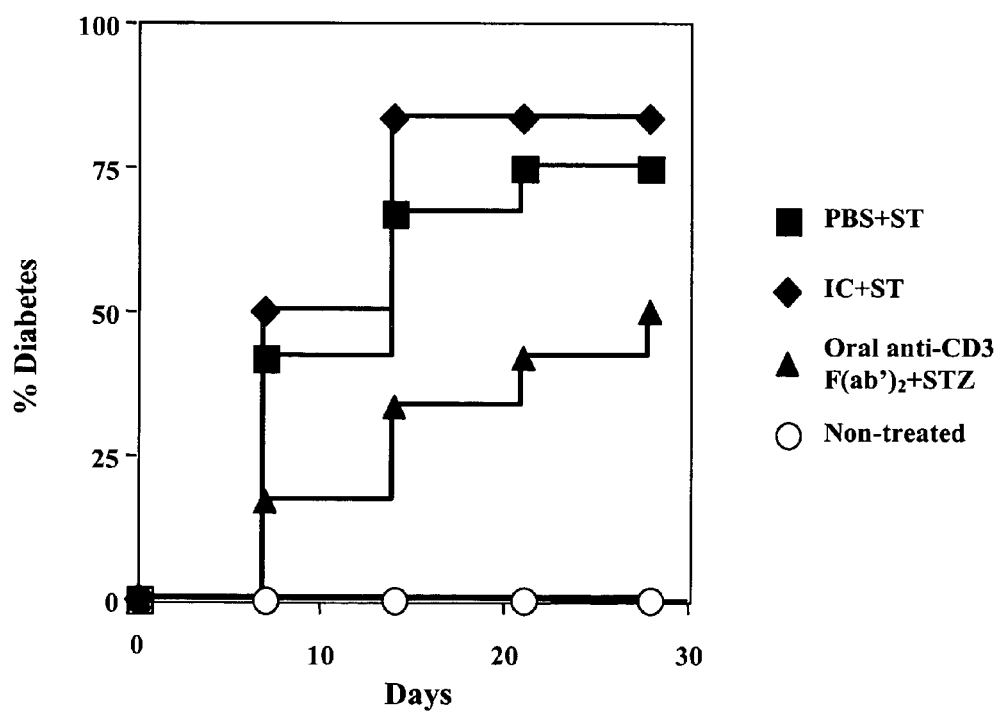
FIG. 20 is a line graph illustrating the effect of PBS (filled squares), isotype control (filled diamonds), or anti-CD3 antibodies (filled triangles) on the incidence of diabetes in streptozotocin-treated mice over a period of 30 days.
Figure 21:
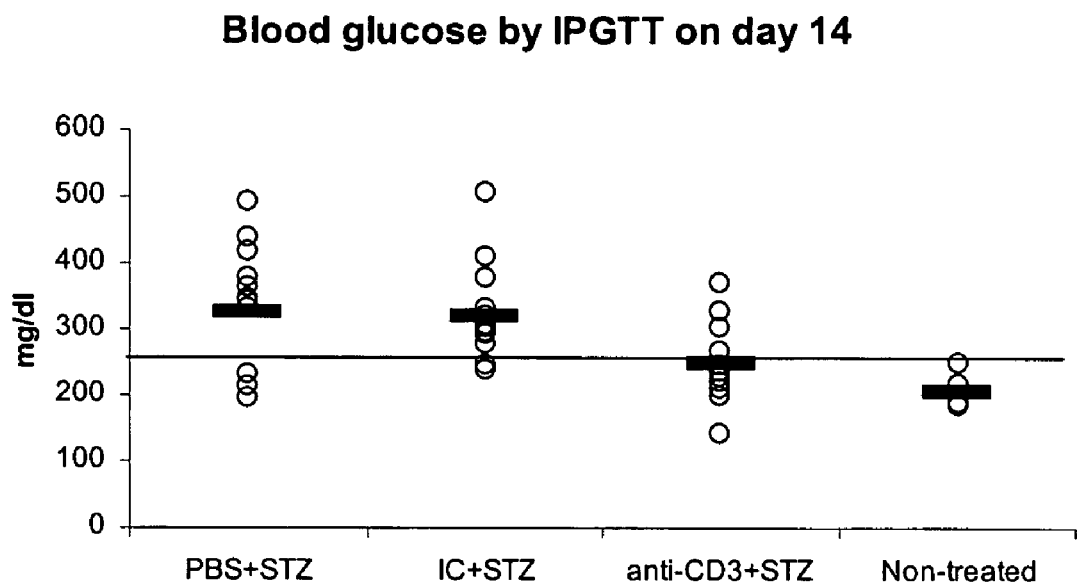
FIG. 21 is a graph showing the mean blood glucose levels at day 14 in the animals in the four groups shown in FIG. 20.

The results are shown in FIGS. 20 and 21. Orally administered anti-CD3 F(ab')₂ was effective in reducing the incidence of STZ-induced diabetes in these mice, and also in delaying the onset of diabetes.

Example 20

Effect of Mucosal Administration of Anti-CD3 Antibody on Collagen Induced Arthritis (CIA)

To evaluate the effect of orally administered anti-CD3 antibodies on autoimmune/rheumatoid arthritis (RA), a collagen induced animal model was used. This animal model of arthritis is an autoimmune model that in many ways resembles RA, as described in Myers et al., Life Sci. 61(19):1861-78 (1997). DBA/1 male mice (Jackson Laboratory, Bar Harbor, Me.) at 6-8 weeks of age were used in this study.

The mice were treated with anti-CD3 F(ab')₂ (Bio-express), or Isotype control (IC) F(ab')₂ (JAX Immunoresearch, Bar Harbor, Me.). Mice were fed (5 μg/feeding, 5 times on consecutive days) or nasally treated (0.5 μg/treatment, 3 times every other day) with anti CD3 antibodies (clone 2CII) or F(ab')₂ preparation, PBS, isotype control antibody or F(ab')₂ isotype control (IC). Each control or treatment group contained 10 mice.

Two days after the last treatment, the mice were immunized intradermally in 5 sites at the base of the tail with 100 μg chicken collagen type II emulsified with Complete Freund's Adjuvant (Difco Labs) containing 50 μg Mycobacterium Tuberculosis (H37RA).

Three weeks later the mice were boosted with a 100 μg of soluble collagen type II by intraperitoneal (I.P.) injection.

Starting one week after the booster, the mice were observed twice a week for the presence of distal joint swelling and erythema. Typically, mice start to show the first symptoms one week after the booster and disease severity continues to exacerbate for more than 80 days. Each limb was scored on a scale of 0 to 4, as follows:
0—absence of arthritis
1—erythema and mild swelling of the tarsus
2—moderate erythema and swelling of the tarsus and ankles
3—severe swelling of the tarsus and ankles
4—ankylosis and bony deformity The Maximum Arthritic Index (MAI) for each mouse is obtained by summing the highest score recorded for each limb (0=no disease, 16 being the highest possible score). The MAI for each group was calculated according to the Mean MAI.

Figure 22A:
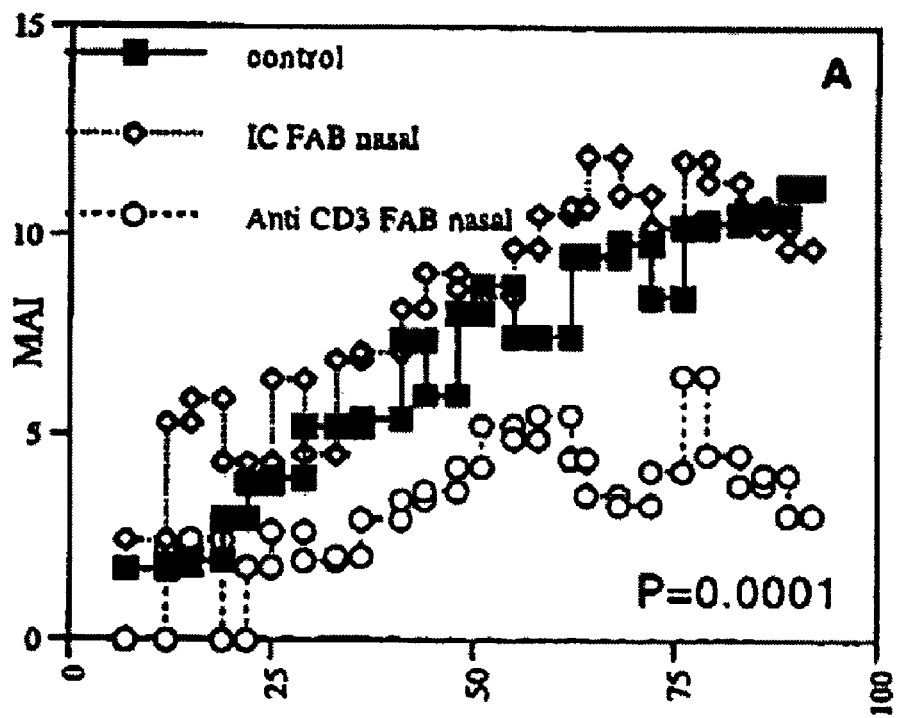
FIG. 22A is a line graph showing Maximum Arthritic Index (MAI) in control mice (filled squares), mice treated with isotype control F(ab')$_2$ (open diamonds), and mice treated with anti-CD3 F(ab')$_2$ (open circles).
Figure 22B:
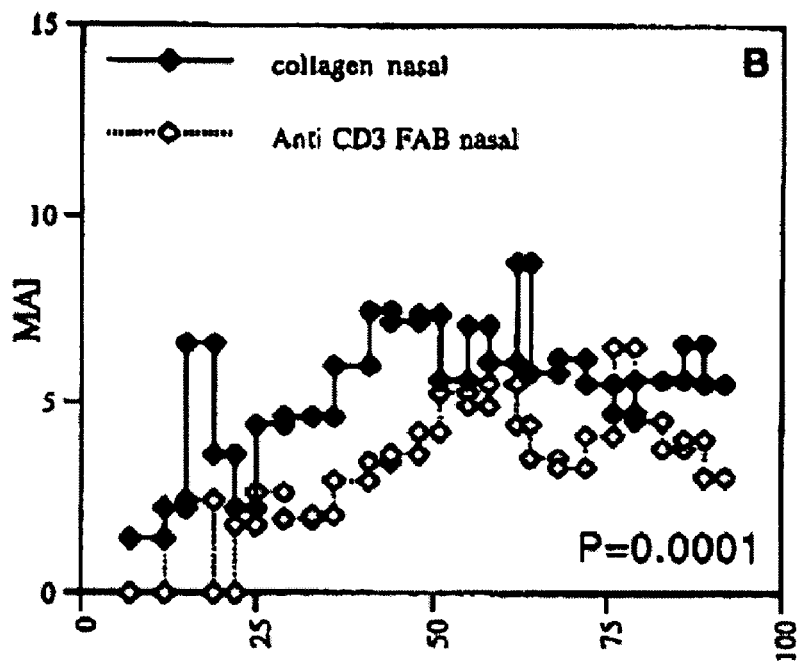
FIG. 22B is a line graph showing Maximum Arthritic Index (MAI) in mice treated with nasal collagen (filled diamonds), and mice treated with nasal anti-CD3 F(ab')$_2$ (open diamonds).
Figure 22C:
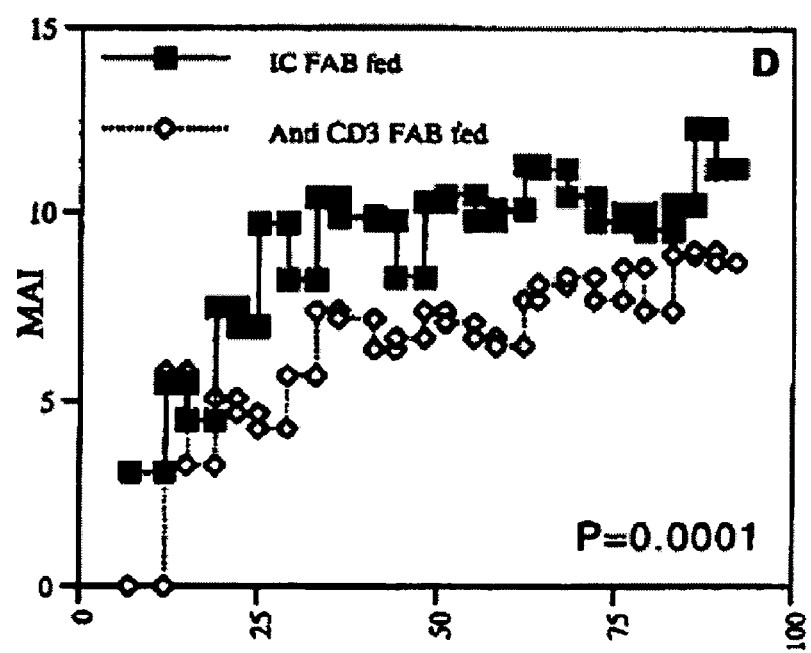
FIG. 22C is a line graph showing Maximum Arthritic Index (MAI) in mice treated with oral isotype control F(ab')$_2$ (filled squares), and mice treated with oral anti-CD3 IgG F(ab')$_2$ (open circles).
Figure 23A:
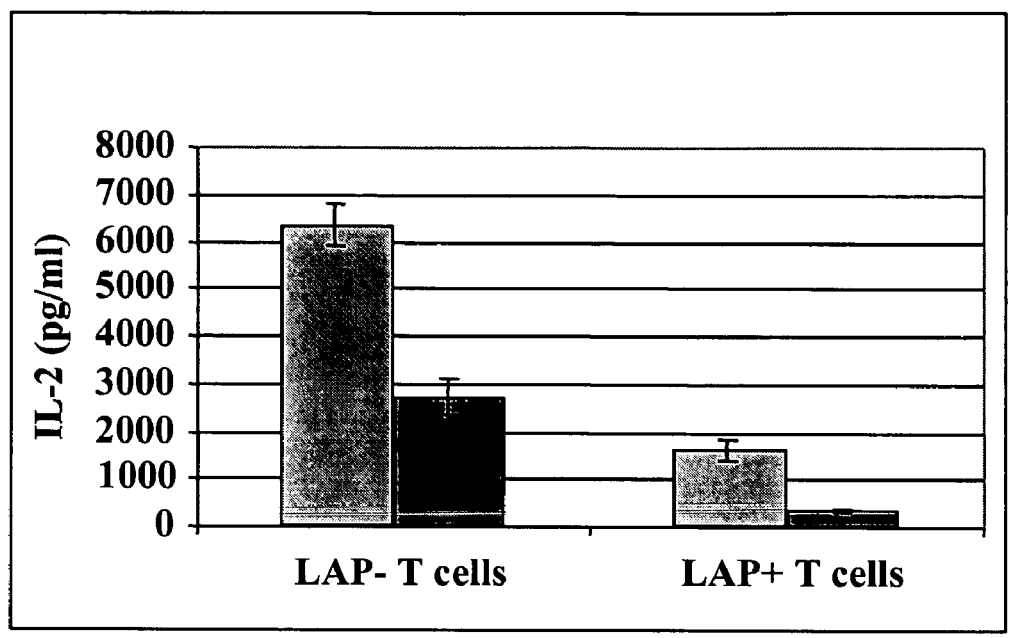
FIG. 23A is a bar graph showing IL-2 secretion in latency associated peptide (LAP)+ and LAP– T cells in mice fed with anti-CD3 (dark gray bars) or isotype control (light gray bars).
Figure 23B:
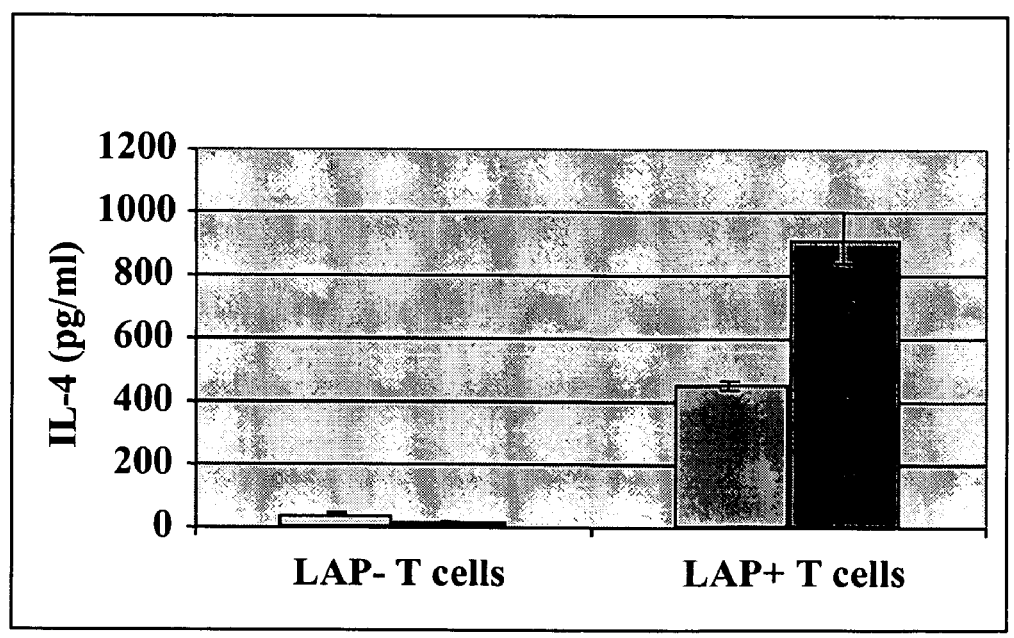
FIG. 23B is a bar graph showing IL-4 secretion in latency associated peptide (LAP)+ and LAP– T cells in mice fed with anti-CD3 (dark gray bars) or isotype control (light gray bars).
Figure 23C:
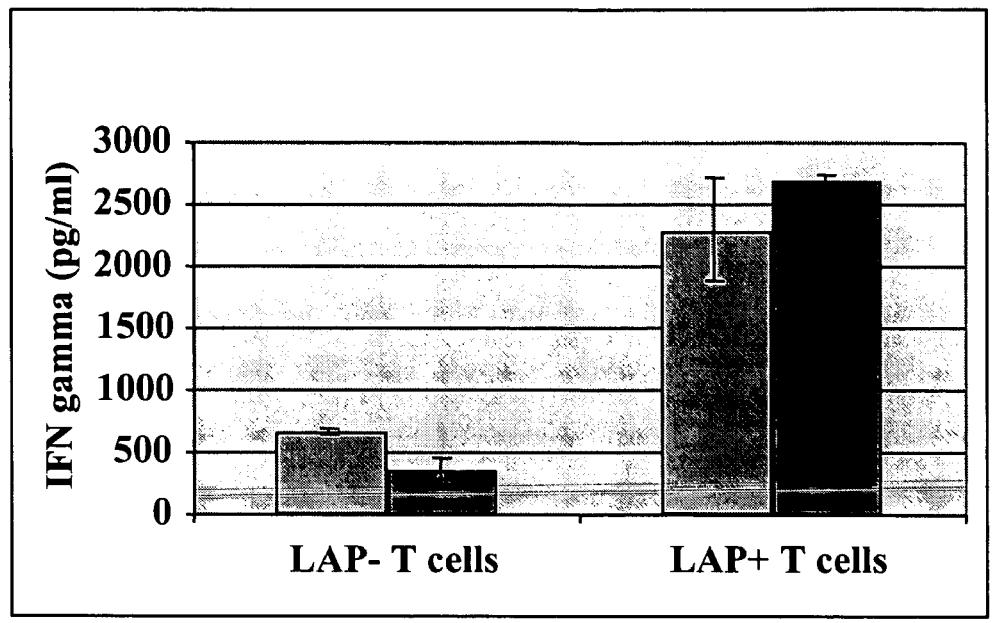
FIG. 23C is a bar graph showing IFN-gamma secretion in latency associated peptide (LAP)+ and LAP– T cells in mice fed with anti-CD3 (dark gray bars) or isotype control (light gray bars).
Figure 23D:
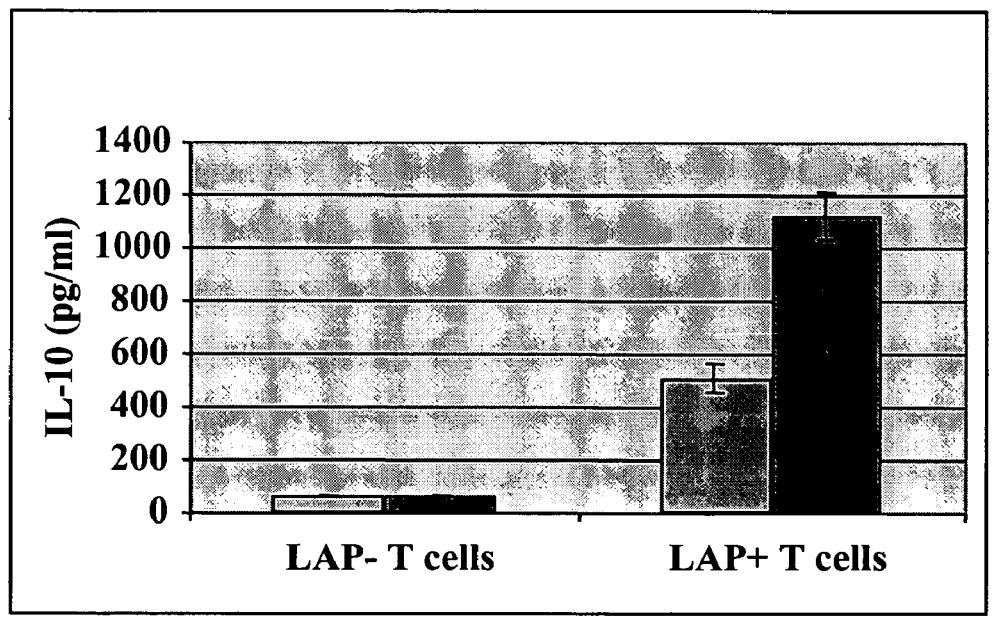
FIG. 23D is a bar graph showing IL-10 secretion in latency associated peptide (LAP)+ and LAP– T cells in mice fed with anti-CD3 (dark gray bars) or isotype control (light gray bars).

The results are shown in FIGS. 22A-C. Mice fed or nasally treated with anti-CD3 F(ab')₂ prior to CIA induction had a significantly lower disease score as compared to either control (PBS treated mice) or isotype control treated mice (FIGS. 22A and 22C). These results indicate that the nasally administered anti CD3 F(ab')₂ generated a better response than the orally administered anti-CD3 F(ab')₂ preparation (FIGS. 22A and 22C). Mice nasally treated with Anti-CD3 F(ab')₂ scored significantly lower (less arthritis) than mice treated with collagen (oral treatment with collagen), although both showed lower scores than control treated mice (FIG. 22B).

These results demonstrate that nasally and orally administered anti-CD3 F(ab')₂ are effective in an in vivo model of autoimmune arthritis.

Example 21

LAP+ Cells in MLN and Peyer's Patch Increase after Feeding with Oral Anti-CD3 Whole IgG Latency Associated Peptide (LAP) is associated with the secretion of functional TGFβ. LAP+ cells are regulatory, and secrete TGFβ (Oida et al., J. Immunol. 170(5):2516-22 (2003)). These cells have been shown to have an immune regulatory effect in humans (Nakamura et al., J. Immunol. 172(2):834-42 (2004)), and are important in suppression of inflammatory disease (La Cava et al., J. Immunol. 173(5): 3542-8 (2004); Ostroukhova, J. Clin. Invest. 114:28 (2004)). The experiments described in this example demonstrate the effect of oral anti-CD3 on LAP+ cells.

Mice were fed with 5 μg of anti-CD3 or isotype control Ab for 5 consecutive days. 24 hours after the last feeding, freshly prepared cells were stained and analyzed by flow cytometry.

TABLE 3

|  | PBS | Isotype Control | Anti-CD3 |
|---|---|---|---|
| Spleen | | | |
| % CD3 among lymphocytes | 42.6 ± 5.7 | 44.7 ± 6.0 | 43.0 ± 6.5 |
| % CD25 + CD4 + cells among CD4 + cells | 13.1 ± 1.6 | 12.6 ± 1.9 | 14.1 ± 2.3 |
| % LAP + cells among CD3 + cells | 8.7 ± 1.1 | 8.3 ± 0.9 | 9.9 ± 1.5 |
| % LAP + cells among CD4 + cells | 4.7 ± 0.6 | 5.1 ± 0.8 | 6.3 ± 1.6**, # |
| Mesenteric LN | | | |
| % CD3 among lymphocytes | 76.2 ± 3.4 | 79.0 ± 2.6 | 78.5 ± 3.30 |
| % CD25 + CD4 + cells among CD4 + cells | 11.5 ± 1.7 | 10.6 ± 1.3 | 11.0 ± 2.0 |
| % LAP + cells among CD3 + cells | 3.0 ± 0.5 | 3.4 ± 0.5 | 5.2 ± 2.0**, ## |
| % LAP + cells among CD4 + cells | 2.0 ± 0.5 | 2.1 ± 0.4 | 3.4 ± 0.9**, ## |
| Peyer's Patch | | | |
| % CD3 among lymphocytes | 39.3 ± 3.4 | 43.0 ± 6.4 | 39.6 ± 5.0 |
| % CD25 + CD4 + cells among CD4 + cells | 14.0 ± 1.8 | 13.1 ± 2.1 | 15.4 ± 3.2 |
| % LAP + cells among CD3 + cells | 8.6 ± 1.0 | 8.8 ± 1.5 | 11.1 ± 2.4*, # |
| % LAP + cells among CD4 + cells | 3.7 ± 0.7 | 3.4 ± 0.8 | 4.6 ± 1.4*, # |

**p < 0.01 as compared with PBS-fed group.
*p < 0.05 as compared with PBS-fed group.
p < 0.01 as compared with isotype control-fed group.
p < 0.05 as compared with isotype control-fed group.

These results demonstrate that feeding anti-CD3 antibody increases regulatory cells, which suppress disease. The increase in these LAP+ cells can be used to measure the immunological effect of anti-CD3 administration, thus, an increase in LAP+ cells in the bloodstream can be used to detect the therapeutic effect of the oral or mucosal administration of anti-CD3 antibody.

Example 22

Cytokine Production from LAP+ and LAP− T Cells Before and after Administration of Oral Anti-CD3

To evaluate the effect of oral anti-CD3 on cytokine production, mice were fed with 5 μg of anti-CD3 or isotype control Ab for 5 consecutive days. 24 hours after the last feeding, LAP+ and LAP− T cells were prepared and stimulated with plate bound anti-CD3 (coated at 10 μg/ml).

The results, shown in FIGS. 23A-D, in combination with the results discussed in Example 21, demonstrate that administration of anti-CD3 antibodies results in an increase in LAP+ cells, which results in an increase in TGFβ and IL-10 secretion. Thus, feeding anti-CD3 antibody increases populations of disease-suppressing regulatory cells. The increase in these LAP+ cells, and the increase in TGFβ and IL-10 production, can be used to measure the immunological effect of anti-CD3 administration and thus to detect and evaluate the therapeutic effect of the oral or mucosal administration of anti-CD3 antibody.

Example 23

In Vitro Suppressive Activity of LAP+ Cells and Oral Administration of Anti-CD3 Antibody To evaluate the effect on the in vitro suppressive activity of LAP+ Cells after oral administration of anti-CD3 antibody, mice were fed with 5 μg of anti-CD3 or isotype control Ab for 5 consecutive days. 24 hours after the last feeding, LAP+ T cells were prepared and their suppressive activity was examined in cultures of CD4+CD25-LAP− responder cells stimulated with soluble anti-CD3 (1 mg/ml) plus T-depleted APC from naïve mice.

Figure 24:
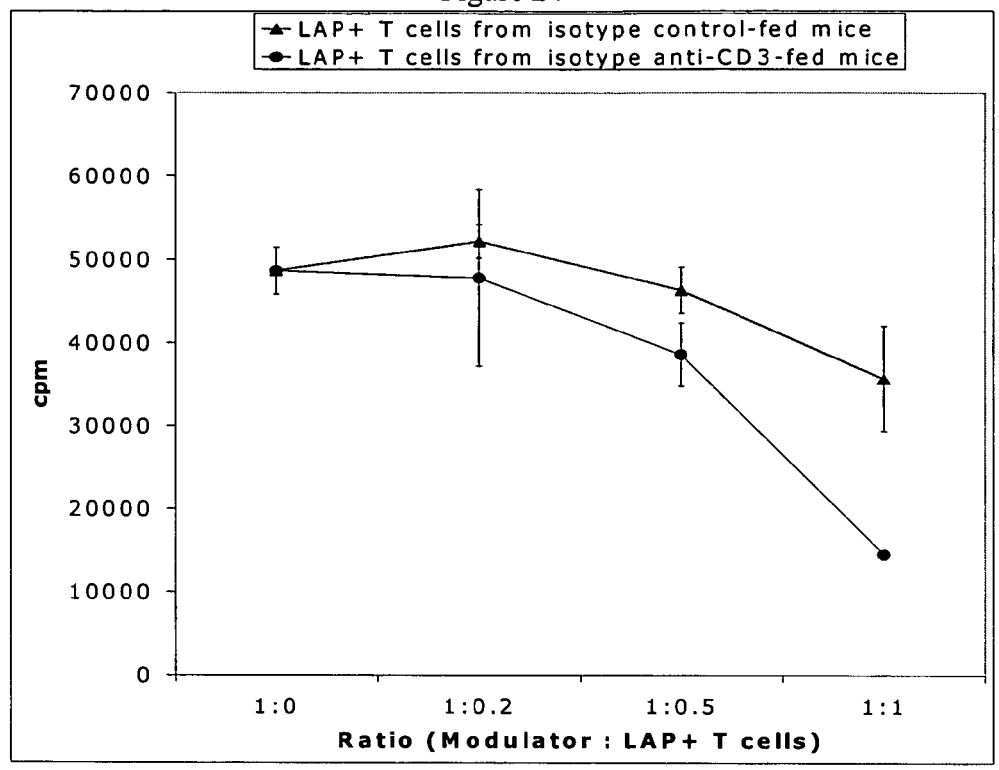
FIG. 24 is a line graph showing levels of LAP+ T cells in mice fed with isotype control antibody (triangles) or anti-CD3 antibody (circles), at different ratios of modulator to LAP+ cells.

The results, shown in FIG. 24, illustrate that the in vitro suppressive activity of LAP+ cells was enhanced after the feeding.

Example 24

Effect of Recombinant LAP In Vitro Suppressive Activity of LAP+ Cells

Figure 25:
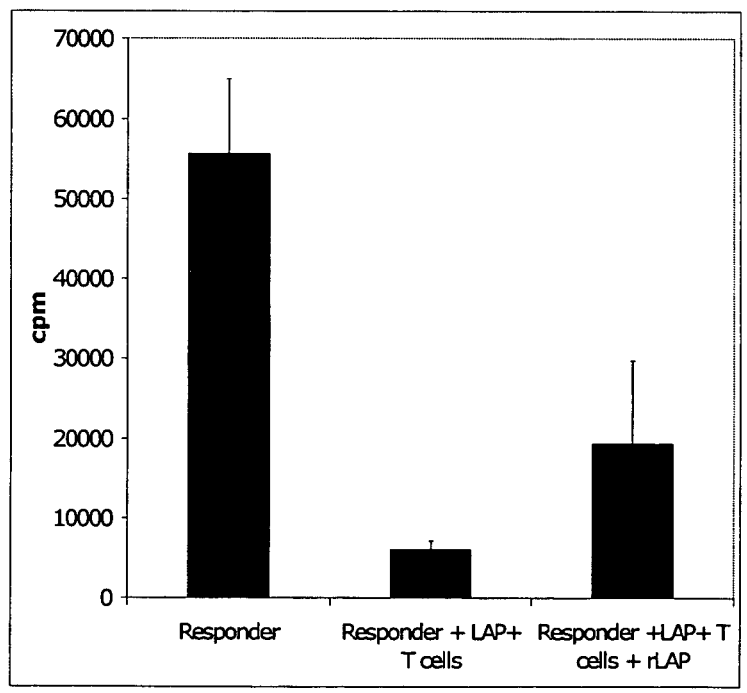
FIG. 25 is a bar graph showing the effect on suppressive activity of LAP+ T cells co-cultured with CD4+CD25-LAP– cells from naïve mice with or without 10 mg/ml of recombinant LAP (rLAP).

To evaluate the effect on the in vitro suppressive activity of LAP+ cells, LAP+ T cells from fed mice were co-cultured with CD4+CD25-LAP− cells from naïve mice with or without 10 mg/ml of recombinant LAP. The results, shown in FIG. 25, demonstrate that the in vitro suppressive activity of LAP+ cells from fed mice was partially reversed by recombinant LAP.

Example 25

Adoptive Transfer of T Cells from Mesenteric Lymph Nodes

Figure 26:
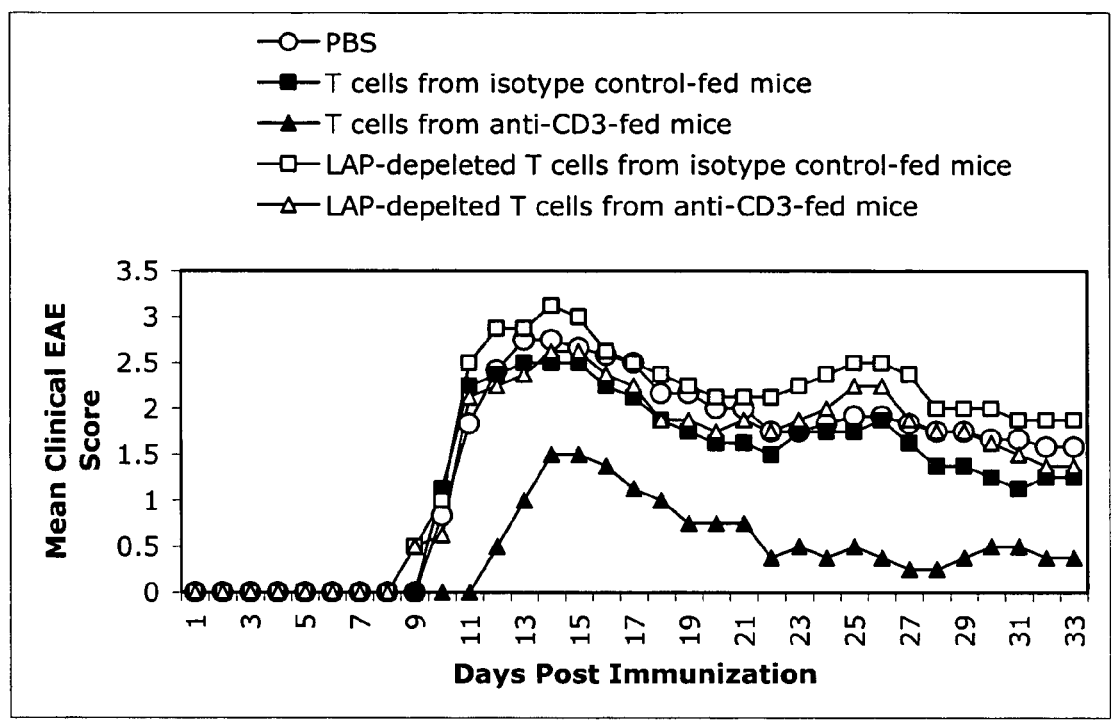
FIG. 26 is a line graph showing the effect on mean clinical EAE score of transplantation of T cells including LAP+ cells from isotype control fed mice (filled squares) or anti-CD3 fed mice (filled triangles), versus LAP-depleted T cells from isotype control fed mice (open squares) or anti-CD3 fed mice (open triangles).

To determine whether the protective effects of the administration of oral anti-CD3 can be adoptively transferred, donor SJL/J mice were fed with 5 μg of anti-CD3 or isotype control Ab for 5 consecutive days. Their mesenteric lymph nodes were removed 48 hours after the last feeding, and purified T cells or LAP-depleted T cells were injected intravenously to naïve SJ/J mice. Recipient mice were immunized with 50 mg of PLP139-151 in CFA to induce EAE. The results, shown in FIG. 26, demonstrate that the effects of oral administration can be adoptively transferred by transplantation of LAP+ cells from fed mice.

Example 26

Neutralization of TGF-β Reversed the Disease Inhibition after Oral Administration of Anti-CD3

Figure 27:
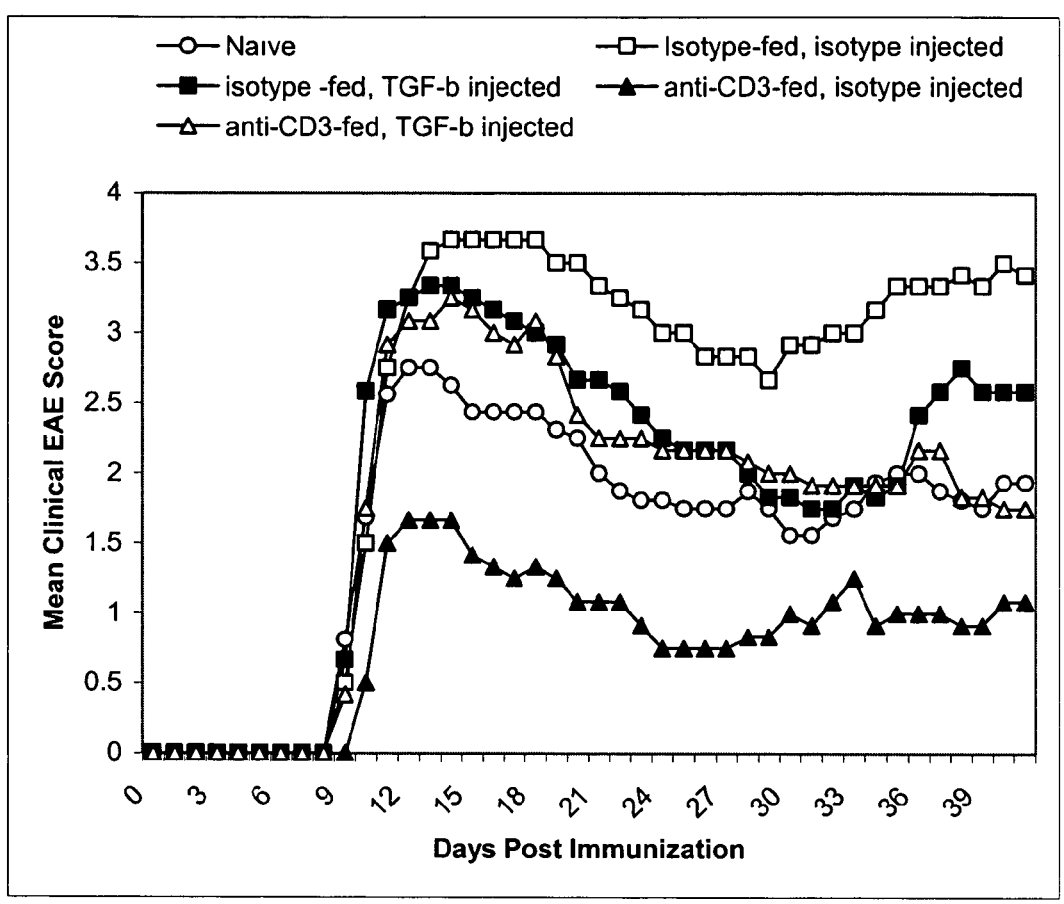
FIG. 27 is a line graph showing the effect of neutralization of TGFβ on mean clinical EAE score. Mice were fed with isotype control and injected with anti-TGFβ Ab (filled squares), fed with anti-CD3 and injected with anti-TGFβ Ab (open triangles), fed with isotype control Ab and injected with isotype control Ab (open squares), or fed with anti-CD3 and injected with anti-isotype control Ab (filled triangles).

To evaluate a possible mechanism by which the disease inhibiting effect of oral anti-CD3 might be occurring, mice were fed with 5 μg of anti-CD3 or isotype control Ab for 5 consecutive days and immunized with 50 mg of PLP139-151 in CFA 48 hours after the last feeding to induce EAE. In combination with the feeding, mice were injected 50 mg of neutralizing anti-TGF-β or isotype control Ab intraperitoneally on days −1, 1, 3, 5 and 7. The results, shown in FIG. 27, demonstrate that neutralization of TGF-β reversed the disease inhibition that results from oral administration of anti-CD3.

Other Embodiments

It is to be understood that while the invention has been described in conjunction with the detailed description thereof, the foregoing description is intended to illustrate and not limit the scope of the invention, which is defined by the scope of the appended claims. For example, other antibodies besides the anti-CD3 antibodies described herein can be administered orally or by other mucosal routes to stimulate the mucosal immune system. For example, in addition to anti-CD3, other antibodies may be given orally or by other mucosal routes to target specific mucosal T cells or immune cell populations in the mucosal immune system, and generate regulatory cells or induce tolerance to treat autoimmune and other inflammatory disorders. Examples include: a) antibodies against co-stimulatory molecules known to be involved in immune regulation such as CD2, ICOS, CD28, CTLA-4, and PD-1 or their ligands; b) antibodies against molecules associated with NK-T cells such as CD94, NK G2; c) antibodies against MHC molecules or their recognition structures such as CD4 and CD8; d) T cell differentiation molecules as TIM molecules; and e) any antibodies or combination thereof that either activate or promote tolerance. Other aspects, advantages, and modifications are within the scope of the following claims.

What is claimed is:

1. A method of treating a disease in a subject, wherein the disease is selected from the group consisting of multiple sclerosis, diabetes, graft-versus-host disease, rheumatoid arthritis, psoriasis, inflammatory bowel disease, lupus, or uveitis, the method comprising administering to the subject a dose of about 1 μg/kg to about 500 μg/kg of an anti-CD3 antibody, or an antigen-binding fragment thereof selected from the group consisting of an F(ab')2 antibody fragment or a CD3-binding dimeric or multimeric scFv, wherein the administering is an oral dosage for ingestion.

2. The method of claim 1, wherein the disease is diabetes.

3. The method of claim 1, wherein the disease is rheumatoid arthritis.

4. The method of claim 1, wherein the disease is multiple sclerosis.

5. The method of claim 1, wherein the antigen-binding fragment is an F(ab')2.

6. The method of claim 1, wherein the disease is lupus.

7. The method of claim 1, wherein the anti-CD3 antibody or antigen-binding fragment thereof is recombinant.

8. The method of claim 1, wherein the anti-CD3 antibody or antigen-binding fragment thereof is humanized.

9. A method of providing an anti-CD3 antibody, or an antigen-binding fragment thereof selected from the group consisting of an F(ab')2 antibody fragment or a CD3-binding dimeric or multimer scFv, to a subject having a disease selected from the group consisting of multiple sclerosis, diabetes, graft-versus-host disease, rheumatoid arthritis, psoriasis, inflammatory bowel disease, lupus, or uveitis, the method comprising administering to the subject an oral dosage form for ingestion suitable to deliver a dosage of about 1 µg/kg to about 500 µg/kg of the anti-CD3 antibody or antigen-binding fragment thereof.

10. The method of claim 1, wherein the anti-CD3 antibody is selected from the group consisting of a monoclonal antibody, a humanized antibody, a human antibody, a chimeric antibody.

11. The method of claim 9, wherein the anti-CD3 antibody is selected from the group consisting of a monoclonal antibody, a humanized antibody, a human antibody, a chimeric antibody.

12. The method of claim 2, wherein the disease is type 1 diabetes.

13. The method of claim 1, wherein the disease is graft-versus-host disease.

14. The method of claim 1, wherein the disease is uveitis.

15. The method of claim 1, wherein the disease is psoriasis.

16. The method of claim 1, wherein the disease is inflammatory bowel disease.

* * * * *